United States Patent [19]
West et al.

[11] Patent Number: 5,648,215
[45] Date of Patent: *Jul. 15, 1997

[54] TELOMERASE DIAGNOSTIC METHODS

[75] Inventors: Michael D. West, San Carlos, Calif.; Jerry Shay, Dallas; Woodring E. Wright, Arlington, both of Tex.

[73] Assignee: Board of Regents, The University of Texas System, Austin, Tex.

[*] Notice: The term of this patent shall not extend beyond the expiration date of Pat. No. 5,489,508.

[21] Appl. No.: 315,216

[22] Filed: Sep. 28, 1994

Related U.S. Application Data

[63] Continuation-in-part of Ser. No. 255,774, Jun. 7, 1994, which is a continuation-in-part of Ser. No. 151,477, Nov. 12, 1993, and Ser. No. 153,051, Nov. 12, 1993, each is a continuation-in-part of Ser. No. 60,952, May 13, 1993, which is a continuation-in-part of Ser. No. 38,766, Mar. 24, 1993, Pat. No. 5,489,508, which is a continuation-in-part of Ser. No. 882,438, May 13, 1992, abandoned.

[51] Int. Cl.$^6$ .............................. C12Q 1/68; C12P 19/34
[52] U.S. Cl. .................... 435/6; 435/91.1; 435/91.5; 435/15; 436/64; 935/77; 935/78
[58] Field of Search .................... 435/6, 91.2, 91.5, 435/83, 184, 94; 436/63, 64, 501; 935/77, 78

[56] References Cited

U.S. PATENT DOCUMENTS

| | | | |
|---|---|---|---|
| 4,737,454 | 4/1988 | Dattagupta et al. | 435/6 |
| 5,489,508 | 2/1996 | West et al. | 435/6 |

FOREIGN PATENT DOCUMENTS

| | | |
|---|---|---|
| 9304546 | 5/1993 | WIPO. |
| 9408053 | 4/1994 | WIPO. |

OTHER PUBLICATIONS

Allsopp et al., "Telomere length predicts replicative capacity of human fibroblasts," *Proc. Ntl. Acad. Sci. USA* 89:10114–10118 (1992).

Cotten, "The in vivo application of ribozymes," *Trends in Biotechnology* 8:174–178 (1990).

Counter et al., "Stabilization of Short Telomeres and Telomerase Activity Accompany Immortalization of Epstein–Barr Virus–Transformed Human B Lymphocytes," *J. Virology* 68:3410–3414 (1994).

Counter et al., "Telomerase activity in human ovarian carcinoma," *Proc. Natl. Acad. Sci. USA* 91:2900–2904 (1994).

Greider and Blackburn, "A telomeric sequence in the RNA of Tetrahymena telomerase required for telomere repeat synthesis," *Nature* 337:331–337 (1989).

Harley et al., "The Telomere Hypothesis of Cellular Aging," *Expermiental Gerontology* 27:375–382 (1992).

Klingelhutz et al., "Restoration of Telomeres in Human Papoillomavirus–Immortalized Human Anogenital Epithelial Cells," *Molecular and Cellular Biology* 14:961–969 (1994).

Shay et al., "Loss of telomeric DNA during aging may predipose cells to cancer (Review)," *Int'l J. Oncology* 3:559–563 (1993).

Strahl and Blackburn, "The effects of nucleoside analogs on telomerase and telomeres in Tetrahymena," *Nucleic Acids Research* 22:893–900 (1994).

Windle and McGuire, "Telomeres: the long and the short of it," *Proceedings of the American Association for Cancer Research* 33:594–595 (1992).

Grieder and Blackburn, "The Telomere Terminal Transferase of Tetrahymena Is a Ribonucleoprotein Enzyme with Two kinds of Primer Specificity", 51 *Cell* 887, 1987.

Blackburn et al., "Recognition and elongation of telomeres by telomerase", 31 *Genome* 553, 1989.

(List continued on next page.)

*Primary Examiner*—Carla J. Myers
*Attorney, Agent, or Firm*—Lyon & Lyon LLP; Kevin Kaster

[57] ABSTRACT

The presence of telomerase activity in a human somatic tissue or cell sample is positively correlated with the presence of cancer and can be used to diagnose the course of disease progression in a patient.

12 Claims, 6 Drawing Sheets

OTHER PUBLICATIONS

Greider, "Telomerase Is Processive", 11 *Molec. and Cell. Biology* 4572, 1991.

Counter et al., "Telomere shortening associated with chromosome instability is arrested in immortal cells which express telomerase activity", 11 *EMBO* 1921, 1992.

Harley, "Telomere loss: mitotic clock or genetic time bomb?", 256 *Mutation Res.* 271, 1991.

Eck and Nabel, "Antisense oligonucleotides for therapeutic intervention", 2, *Opin. Biotech* 897, 1991.

Zahler et al., "Inhibition of telomerase by G-quartet DNA structures", 350 *Nature*, 718, 1991.

Yu and Blackburn, "Developmentally Programmed Healing of Chromosomes by Telomerase in Tetrahymena", 67 *Cell* 823, 1991.

Harley et al., "Telomeres shorten during ageing of human fibroblasts", 345 *Nature* 458, 1990.

Blackburn, "Structure and function of telomeres", 350 *Nature* 569, 1991.

Cech, "Ribozymes and Their Medical Implications", 260 *JAMA* 3030, 1988.

S. Wang and V. Zakian (1990) Nature 345:456. Telomere-telomers recombination provides an express pathway for telomere acquisition.

S. Goldstein (1990) Science 249:1129. Replicative senescence; the human fibroblast comes of age.

J. Smith and R. Whitriey (1980) Science 207:82. Intraclonal variation in proliferative potential of human diploid fibroblasts:stochastle mechanisms for cellular aging.

T. Ohno (1979) Mechanisms of aging and development 11:179. Strict relationship between dialyzed serum concentration and cellular life span in vitro.

L. Hayfliek and P. Moorhead (1961) Experimental Cell Research 25:585. The serial cultivation of human diplolld cell strains.

J. Szostak (1989) Nature 337:303, The beginning of the ends.

G. Jankovic, et al. (1991) Nature 350:197, Telomere loss and cancer.

J. Gall (1990) Nature 344:108. Tying up loose ends.

G. Yu, et al. (1990) Nature 344:126. In vivo alteration of telomere sequences and senescence caused by mutated Tetrahymena telomerase RNAs.

L. Harrington and C. Greider (1991) Nature 353:451. Telomerase primer specificity and chromosome healing.

J. Gray, et al. (1991) Cell 67:807. Cloning and expression of genes for the Oxytricha telomere-binding protein:specific subunit interactions in the telomeric complex.

F. Muller, et al. (1991) Cell 67:815. New telomere formation after developmentally regulated chromosomal breakage during the process of chromosome diminution in *Ascaris lumbricoldes*.

G. Yu and E. Blackburn (1991) Cell 67:823, Developmentally programmed healing of chromosomes by telomerase in Tetrahymeno.

C. Greider (1990) Bioessays 12:363. Telomeres, telomerase and senesence.

B. Henderson, et al. (1990) Biochemistry 29:732. Telomere G-strand structure and function analyzed by chemical protection, base analogue substitution, and utilization by telomerase in vitro.

D. Gottschling, et al. (1990) Cell 63:751, Position effect at *S. cerevisiae* telomeres: reversible repression of Pol II transcription.

V. Lundblad and J. Szosiak (1989) Cell 57:633. A mutant with a defect in telomere elongation leads to senescence in yeast.

E. Blackburn (1984) Annual Reviews In Biochemistry 53:163, The molecular structure of centromeres and telomeres.

A. Olovnikov (1973) J. Theoretical Biology 41:181, A theory of marginotomy.

E. Blackburn (1991) Nature 350:569, Structure and function of telomeres.

H. Cooke and B. Smith (1986) CSHSQB LI:213, Variability at the telomeres of the human X/Y pseudosutosomal region.

C. Greider (1991) Cell 67:645. Chromosome first aid.

G. Morin (1989) Cell 59:521. The human telomere terminal transferase enzyme is a ribonucleoprotein that synthesizes TTAGGG repeats.

Ham and McKeehan (1979) Methods in Enzymology LVIII:44, Media and growth requirements.

J. Starling, et al. (1990) Nucleae Acids Research 18:6881, Extensive telomere repeat arrays in mouse are hypervariable.

Chadeneau, et al. Cancer Research (1995) 55:2533-2536.

Hiyama et al, Journal National Cancer Institute, (1995) 87:895-902.

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 1:

CCCAATCCGT CGAGCAGAGT TAG    23

( 2 ) INFORMATION FOR SEQ ID NO: 2:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) SEQUENCE DESCRIPTION: SEQ ID NO: 2:

TAACTCTGCT CGACGGATTC CC    22

( 2 ) INFORMATION FOR SEQ ID NO: 3:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 3:

GGGTAACCCT AACCCTAACC C    21

( 2 ) INFORMATION FOR SEQ ID NO: 4:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) SEQUENCE DESCRIPTION: SEQ ID NO: 4:

GGTTAGGGTT AGGGTTAAA    19

( 2 ) INFORMATION FOR SEQ ID NO: 5:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) SEQUENCE DESCRIPTION: SEQ ID NO: 5:

GTTAGGGTTA GGGTTAGG    18

( 2 ) INFORMATION FOR SEQ ID NO: 6:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) SEQUENCE DESCRIPTION: SEQ ID NO: 6:

TTAGGGTTAG GGTTAGGG    18

( 2 ) INFORMATION FOR SEQ ID NO: 7:

( i ) SEQUENCE CHARACTERISTICS:
    ( A ) LENGTH: 18
    ( B ) TYPE: nucleic acid
    ( C ) STRANDEDNESS: single (D) TOPOLOGY: linear (ii) SEQUENCE DESCRIPTION: SEQ ID NO: 7:
AATCCGTCGA GCAGAGTT                                                      18

(2) INFORMATION FOR SEQ ID NO: 8:

(i) SEQUENCE CHARACTERISTICS:
(A) LENGTH: 24
(B) TYPE: nucleic acid
(C) STRANDEDNESS: single
(D) TOPOLOGY: linear (ii) SEQUENCE DESCRIPTION: SEQ ID NO: 8:
CCCTTACCCT TACCCTTACC CTAA                                               24

(2) INFORMATION FOR SEQ ID NO: 9:

(i) SEQUENCE CHARACTERISTICS:
(A) LENGTH: 18
(B) TYPE: nucleic acid
(C) STRANDEDNESS: single
(D) TOPOLOGY: linear (ii) SEQUENCE DESCRIPTION: SEQ ID NO: 9:
CCCTAACCCT AACCCTAA                                                      18

(2) INFORMATION FOR SEQ ID NO: 10:

(i) SEQUENCE CHARACTERISTICS:
(A) LENGTH: 24
(B) TYPE: nucleic acid
(C) STRANDEDNESS: single
(D) TOPOLOGY: linear (ii) SEQUENCE DESCRIPTION: SEQ ID NO: 10:
CCCTAACCCT AACCCTAACC CTAA                                               24

(2) INFORMATION FOR SEQ ID NO: 11:

(i) SEQUENCE CHARACTERISTICS:
(A) LENGTH: 24
(B) TYPE: nucleic acid
(C) STRANDEDNESS: single
(D) TOPOLOGY: linear (ii) SEQUENCE DESCRIPTION: SEQ ID NO: 11:
GCGCGGCTCT AACTCTAACT CTAA                                               24

(2) INFORMATION FOR SEQ ID NO: 12:

(i) SEQUENCE CHARACTERISTICS:
(A) LENGTH: 47
(B) TYPE: nucleic acid
(C) STRANDEDNESS: single
(D) TOPOLOGY: linear (ii) SEQUENCE DESCRIPTION: SEQ ID NO: 12:
AATCCGTCGA GCAGAGTTAG CCCGGTTAGG GTTAGGGTTA GCCGCGC

TELOMERASE DIAGNOSTIC METHODS

The present application is a continuation-in-part of U.S. patent application Ser. No. 08/255,774, filed Jun. 7, 1994, which is a continuation-in-part of Ser. Nos. 08/151,477 and 08/153,051, both of which were filed 12 Nov. 1993, which are continuations-in-part of Ser. No. 08/060,952, filed 13 May 1993, which is a continuation-in-part of Ser. No. 08/038,766, filed 24 Mar. 1993, which is a continuation-in-part of now abandoned Ser. No. 07/882,438, filed 13 May 1992. Each of the foregoing patent applications is incorporated herein by reference.

STATEMENT OF GOVERNMENT RIGHTS

A portion of the research and results described herein was supported by NIH grant Nos. AG07992 and CA50195, and the U.S. government may therefore have certain rights regarding the invention disclosed herein.

BACKGROUND OF THE INVENTION

1. Field of Invention

The present invention relates to telomerase, a ribonucleoprotein enzyme involved in telomere DNA synthesis, and provides assays and protocols for identifying and measuring telomerase activity and correlating that activity with disease conditions. The invention provides methods and compositions relating to the fields of molecular biology, chemistry, pharmacology, and medical diagnostic and prognostic technology.

2. Description of Related Disclosures

Telomeres are specialized structures at the ends of eukaryotic chromosomes and appear to function in chromosome stabilization, positioning, and replication (Blackburn and Szostak, 1984, *Ann. Rev. Biochem.* 53:163-194; Zakian, 1989, *Ann. Rev. Genetics* 23:579-604; Blackburn, 1991 *Nature* 350:569-573). In all vertebrates, telomeres consist of hundreds to thousands of tandem repeats of 5'-TTAGGG-3' sequence and associated proteins (Blackburn, 1991; Moyzis et al., 1988, *Proc. Natl. Acad. Sci.* 85:6622-6626). Southern blot analysis of chromosome terminal restriction fragments (TRF) provides the composite lengths of all telomeres in a cell population (Harley et al., 1990, *Nature* 345:458-460; Allsopp et al., 1992, *Proc. Natl. Acad. Sci. USA* 89:10114-10118; Vaziri et al., 1993, *Am. J. Human Genetics* 52:661-667). In all normal somatic cells examined to date, TRF analysis has shown that the chromosomes lose about 50-200 nucleotides of telomeric sequence per cell division, consistent with the inability of DNA polymerase to replicate linear DNA to the ends (Harley et al., 1990; Allsopp et al., 1992; Vaziri et al., 1993; Watson, 1972, *Nature New Biology* 239:197-201).

This shortening of telomeres has been proposed to be the mitotic clock by which cells count their divisions (Harley, 1991, *Mut. Res.* 256:271-282), and a sufficiently short telomere(s) may be the signal for replicative senescence in normal cells (Allsopp et al., 1992; Vaziri et al., 1993; Hastie et al., 1990, *Nature* 346:866-868; Lindsey et al., 1991, *Mut. Res.* 256:45-8; Wright and Shay, 1992, *Trends Genetics* 8:193-197). In contrast, the vast majority of immortal cells examined to date show no net loss of telomere length or sequence with cell divisions, suggesting that maintenance of telomeres is required for cells to escape from replicative senescence and proliferate indefinitely (Counter et al., 1992, *EMBO* 11:1921-1929; Counter et al., 1994, *Proc. Natl. Acad. Sci. USA* 91:2900-2940).

Telomerase, a unique ribonucleoprotein DNA polymerase, is the only enzyme known to synthesize telomeric DNA at chromosomal ends using as a template a sequence contained within the RNA component of the enzyme (Greider and Blackburn, 1985, *Cell* 43:405-413; Greider and Blackburn, 1989, *Nature* 337:331-337; Yu et al., 1990, *Nature* 344:126-132; Blackburn, 1992, *Ann. Rev. Biochem.* 61:113-129). With regard to human cells and tissues, telomerase activity has been identified in immortal cell lines and in ovarian carcinoma but has not been detected in mortal cell strains or in normal non-germline tissues (Counter et al., 1992; Counter et al., 1994; Morin, 1989, *Cell* 59:521-529). Together with TRF analysis, these results suggest telomerase activity is directly involved in telomere maintenance, linking this enzyme to cell immortality.

Scientists have therefore proposed that senescence, or mortality stage 1 (M1), occurs when there are on average several kilobases of telomeric repeats remaining and involves the anti-proliferative actions of tumor suppressor gene products such as pRb and p53 (Shay et al., 1993, *Oncogene* 8:1407). Mutations in these genes, or expression of viral transforming genes that block the action of these genes, permit cells to undergo additional divisions in the absence of telomerase until the telomeres reach a critically short length at crisis, or mortality stage 2 (M2). See Wright et al., 1989, *Mol. Cell. Biol.* 9:3088. At crisis, there is destabilization of chromosomes resulting in an increase in the frequency of dicentric chromosomes and cessation of cell proliferation. Development of an immortalized cell line after crisis is dependent on expression of telomerase activity. After crisis, telomerase can stabilize telomere length and permit indefinite cell division (Blackburn, 1994, *Cell* 77:621).

Methods for detecting telomerase activity, as well as for identifying compounds that regulate or affect telomerase activity, together with methods for therapy or diagnosis of cellular senescence and immortalization by controlling or measuring telomere length and telomerase activity, have also been described. See PCT patent publication No. 93/23572, published Nov. 25, 1993, incorporated herein by reference. The identification of compounds affecting telomerase activity provides important benefits to efforts at treating human disease. Compounds that inhibit telomerase activity can be used to treat cancer, as cancer cells express and require telomerase activity for immortality, and normal human somatic cells do not express telomerase activity at detectable levels. Compounds that stimulate or activate telomerase activity can be used to treat age-related diseases and other conditions relating to cell senescence.

New and improved methods for screening to identify compounds that modulate telomerase activity as well as for measuring telomerase activity in a sample have been developed; see, e.g., U.S. patent application Ser. No. 08/315,214, filed Sep. 28, 1994 inventors Calvin B. Harley, Nam Woo Kim, and Scott Weinrich, incorporated herein by reference. Other methods for assaying telomerase activity in cell samples rely on the incorporation of radioactively labeled nucleotides into a telomerase substrate (Morin, 1989). The conventional assay uses an oligonucleotide substrate, a radioactive deoxyribonucleoside triphosphate (dNTP) for labeling, and gel electrophoresis for resolution and display of products. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists have found that the presence of telomerase activity in somatic tissues is positively correlated with cancer. There remains a need, however, for diagnostic methods that enable the physician to correlate the presence of telomerase activity in a sample with the likelihood that a particular type of cancer is likely to be invasive or metastasize or recur, to assess whether cancer cells remain in a patient after surgery, chemotherapy, or other treatments, and to diagnose a patient's predisposition to cancer, and this invention meets that need.

SUMMARY OF THE INVENTION

The present invention provides diagnostic methods for determining whether a cell sample contains telomerase activity and for correlating the presence of telomerase activity with a variety of cancers and disease progression. The basic method involves the following steps: (a) preparing a cell extract from a tissue or cell sample; (b) incubating an aliquot of said cell extract in a reaction mixture comprising a telomerase substrate and a buffer in which telomerase can catalyze the extension of said telomerase substrate; (c) determining whether said telomerase substrate has been extended in step (b) by addition of telomeric repeat sequences; and (d) correlating presence of cancerous cells in said sample with the addition of telomeric repeat sequences to said telomerase substrate and absence of cancerous cells in said sample with no addition of telomeric repeat sequences to said telomerase substrate.

The method is especially useful for diagnosing cancers of the breast and prostate and for predicting disease progression of cancers in those tissues. The method can also be applied to any tissue samples taken from sites adjacent to a tumor to determine whether all tumor cells have been removed. The method can also be used to assess the likelihood that an individual previously diagnosed as having axillary node negative breast cancer will suffer a recurrence of cancer. In similar fashion, the method can be used to assess the likelihood that an individual previously diagnosed as having benign prostatic hyperplasia or prostatic intraepithelial neoplasia will develop prostate cancer. Thus, the method can be performed using samples such as peritoneal fluid to detect ovarian cancer, tissue removed as a result of a transurethral resection of the prostate to detect prostate cancer, fluid from the mammary duct to detect breast cancer, pleural effusions to detect lung cancer, and urine or semen to detect bladder cancer.

In a general aspect, the present invention provides a diagnostic method that allows the physician to make an accurate prognosis of the course of disease progression in a cancer patient, particularly with respect to whether a tumor is likely to metastasize to distant sites or invade adjacent tissue. In this aspect of the invention, the presence of telomerase activity in tumor cells derived from a patient is positively correlated with a negative prognosis, i.e., the cancer is likely to be invasive or metastasize and merits aggressive therapeutic intervention to prevent recurrence of disease.

These and other aspects of the invention are described in more detail below, beginning with a brief description of the accompanying drawings.

BRIEF DESCRIPTION OF THE DRAWINGS

In FIG. 1, part A, CHAPS-extracted cell preparations are used in the conventional assay, and the results show the extracts perform as expected. See Example 1, below. In FIG. 1, part B, the telomerase substrate "TS" (SEQ ID NO.7) is shown together with a TS telomerase extension product (with about 4 telomeric repeat sequences; the number of repeat sequences can vary from extension product to extension product), which is shown duplexed (vertical lines indicate base-pairing and asterisks indicate mismatches, which were incorporated into the design of the primer to minimize interaction of the primer with unextended telomerase substrate) with the "CX" (SEQ ID NO.8) primer. Broken arrows in this Figure represent the potential primer extension products formed during the PCR step; the potential extension product of the CX primer is shown sandwiched between actual and potential TS extension products. FIG. 1, part D, shows the results of multiple control experiments demonstrating that a positive signal in the assay (which is also referred to as the "Telomerase Repeat Amplification Protocol" or "TRAP assay") requires a ribonucleoprotein in an immortal cell extract capable of extending the TS oligonucleotide with three or more 5'-TTAGGG-3' repeats, validating the assay for specific detection of telomerase activity (see Example 2, below). FIG. 1, part E, shows the results of analyzing a variety of samples containing differing levels of telomerase activity to illustrate the increased sensitivity of the method (see Example 2, below)

DESCRIPTION OF THE PREFERRED EMBODIMENTS

The present invention provides novel diagnostic methods for detecting cancer cells and for predicting the course of tumor progression in an individual with cancer. The diagnostic methods involve the detection of telomerase activity and the correlation of the presence of telomerase activity in a cell or tissue sample with cancer and disease progression. While any method for assaying telomerase activity can be employed for purposes of the present invention, a particularly preferred method involves the preparation of a cell extract using a detergent lysis method and the analysis of telomerase activity by the Telomeric Repeat Amplification Protocol (TRAP assay). Thus, for a more complete understanding of the invention, the detergent extraction method and TRAP assay are described in some detail herein.

Example 1, below, describes the detergent-based extraction protocol and demonstrates that telomerase activity, as measured by the conventional assay, is retained in cell extracts prepared according to the method. Example 2, below, describes the TRAP assay and comparative test results using the TRAP assay and the conventional assay. Example 3, below, demonstrates how the TRAP assay can be used to determine whether telomerase activity is present in cell extracts prepared from immortal cell lines and normal somatic cell cultures. Example 4, below, provides a standard protocol for conducting the TRAP assay.

Figure 3:
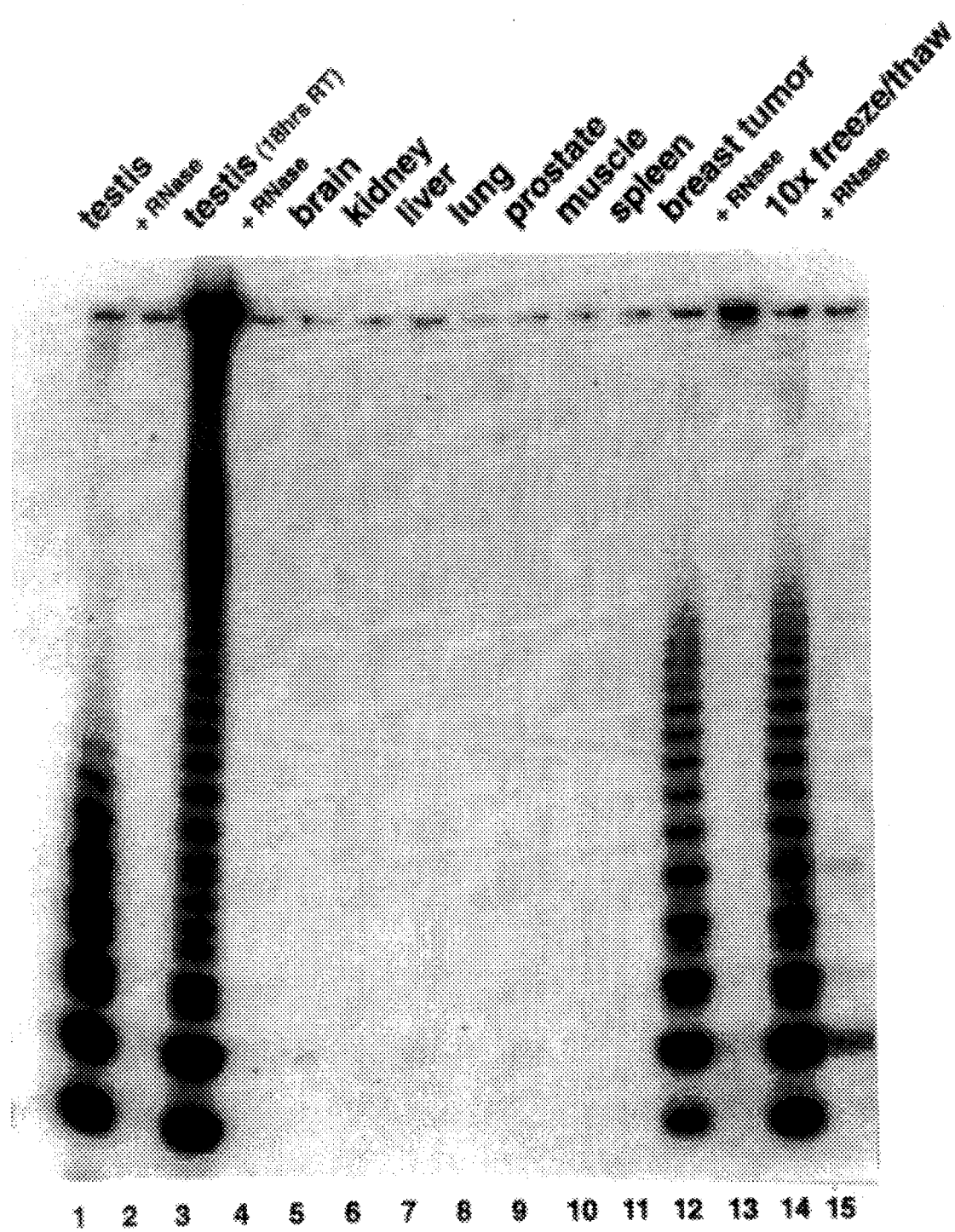
FIG. 3 shows the results of analysis of normal somatic and germline tissues for telomerase activity. Telomerase activity was present in testicular tissue but not in other tissues examined (lanes 1 and 5–11). Pre-incubation of the testicular tissue extract with RNase to destroy the RNA component of telomerase abolished the PCR ladder (lane 2). A portion of the testicular sample was incubated at room temperature for 18 hours and then assayed; the sample retained activity (lane 3). Telomerase activity was still retained in an extract from a human primary breast tumor (lane 12) even after 10 cycles of freeze/thawing (lane 14).

While Examples 1 through 4, below, describe protocols for preparing cell extracts and measuring telomerase activity, the methods of the present invention will typically involve the determination of telomerase activity from cell or tissue samples derived from human patients or histological sections. Example 5, below, describes how such samples are prepared for assay and a series of control experiments demonstrating that the TRAP assay was reliable for analysis of telomerase activity in human tissue samples subjected to a variety of experimental manipulations. In these tests, normal somatic (telomerase negative) and germline (telomerase positive) tissues were obtained from a male who died of natural causes (heart attack). Immediately postmortem this individual was at room temperature for approximately 3 hours and then maintained for an additional 9 hours at 4° C. prior to autopsy. The results of the tests are shown in FIG. 3.

As expected, telomerase activity was present in testicular tissue but not in other tissues examined (lanes 1 and 5–11). Preincubation of the testicular tissue extract with RNase to destroy the RNA component of telomerase abolished the PCR ladder (lane 2). To determine the stability of telomerase activity, a portion of the testicular sample was incubated at room temperature for 18 hours and then assayed; the sample retained activity (lane 3). Telomerase activity was still retained in an extract from a human primary breast tumor (lane 12) even after 10 cycles of freeze/thawing (lane 14). These tests demonstrated that telomerase activity is relatively stable and that negative results are likely to represent the absence of telomerase activity rather than its loss.

The TRAP assay was then used to analyze a variety of cell and tissue samples from cancer patients and non-tumor individuals (see FIG. 4 and Example 5, below). About 54 tissue samples of breast tissue were obtained from 34 different patients. None of the eight samples from non-tumor patients (from reduction or augmentation mammoplasty) was positive, as expected due to the absence of telomerase activity in normal somatic tissue. When breast tumor tissue extracts were examined for telomerase activity, 18 of the 20 samples were positive for telomerase activity. The absence of telomerase activity in a breast tumor tissue sample is diagnostic of a benign tumor or an early stage malignant tumor and correlates with a positive prognosis suggesting treatment will be effective in eliminating all tumor cells.

In similar fashion, analysis of apparently normal tissue adjacent to a tumor site with the diagnostic method of the invention also allows the physician to make more informed decisions about the likely course of disease progression in a patient. When 20 samples of supposedly normal tissue adjacent to breast tumor sites were analyzed, 2 samples were positive for telomerase activity. The positive samples were from axillary-node positive patients, whose prognosis is generally poor, confirming the utility of the present method for prognostic purposes. The diagnostic method of the invention allows the physician to correlate the presence of telomerase activity in such samples with the presence of malignant tumor cells in tissues adjacent to the tumor site. Such a correlation suggests a negative prognosis for the course of disease progression in the patient and allows the physician to treat the tumor more aggressively than might otherwise be the case, given that, by conventional diagnostic methods, the adjoining tissue appears normal.

One such conventional method for making a prognosis in the case of an individual with a breast tumor is the histological analysis of axillary node tissue for abnormal cells. While a diagnosis that the axillary node is negative for the presence of abnormal cells is generally correlated with a positive prognosis, epidemiology indicates that 25–30% of axillary node-negative patients will have recurrence of breast cancer. The present invention provides a diagnostic method for more accurately predicting whether axillary node-negative individuals previously diagnosed with breast cancer are likely to suffer a recurrence of the disease. Of the 4 axillary-node negative breast tumor cell samples analyzed, one had detectable telomerase activity. The presence of telomerase activity in such samples correlates with a greater likelihood that the disease will recur, suggesting a more aggressive therapeutic treatment regimen.

These and other results of analyzing telomerase activity in human breast tissues are summarized in the table below.

TABLE 1

Telomerase Activity in Human Breast Tissues

| Human Breast | Presence of Telomerase Activity |
| --- | --- |
| Normal breast tissue | 0/8 |
| Primary carcinoma (axillary node-negative) | 1/4 |
| Low grade phyllodes tumor | 1/1 |
| Ductal adenocarcinoma (node-positive) | 16/17 |
| Adjacent "normal tissue" | 2/17 |
| Lobular adenocarcinoma (node-positive) | 2/3 |
| Adjacent normal tissue | 0/2 |
| Metastatic andenocarcinoma (lymph node) | 1/1 |

The results in Table 1 demonstrate that the presence of telomerase activity correlates with the presence of cancer cells in a sample. The results also show that the diagnostic method of the invention can be used to detect the presence of cancer cells in tissue that appears normal by conventional methods.

The present invention provides similarly beneficial diagnostic methods relevant to the detection and treatment of prostate cancer. Samples of normal and abnormal prostate tissue were analyzed using the TRAP assay. Of the 8 normal prostatic tissues examined, all were negative for telomerase activity. Samples from two adenomatous carcinomas of the prostate were positive. Samples of prostate tissue from individuals with benign prostate hyperplasia (BPH) were also examined, and of the 10 samples examined, 1 was telomerase-positive, indicating that cancer cells were present. Thus, the present invention provides a diagnostic method for assessing whether an individual with BPH has or is likely to develop prostate cancer, which method comprises the steps of analyzing a prostate tissue sample for the presence of telomerase activity, and correlating the presence of telomerase activity with the presence of cancer cells.

In similar fashion, the present invention provides a diagnostic method for assessing whether an individual with prostatic intraepithelial neoplasia (PIN) has or is likely to develop cancer. While there is no direct evidence to date that PIN is an obligate precursor of adenocarcinoma, there is circumstantial evidence for the premalignant nature of PIN (see Garnick, 1994, *Scientific American* 279(4):72, and Jones and Young, 1994, *Am. J. Clin. Pathol.* 101:48). PIN type 3 (PIN3) has malignant cytological features and is often found adjacent to infiltrating adenocarcinoma. Individuals with PIN have abnormal cell differentiation, increased cell proliferation, abnormal DNA content, and often have elevated ras mRNA expression. PIN3 is found eight times more frequently in association with carcinoma than without tumor. When 5 samples of prostatic tissue from PIN3 individuals were examined with the TRAP assay, 3 of the samples had detectable telomerase activity. Individuals with telomerase-positive PIN3 cells are closer to overt malignance than those with telomerase-negative cells, and the presence of telomerase activity in such samples is diagnostic of a high probability for cancer progression.

While the diagnostic methods of the invention offer particular benefit to the prognosis of disease progression in individuals suffering from breast or prostate cancer, the present methods are also valuable in the analysis of other cancers. For instance, normal myometrium (10 samples tested) and the benign uterine tumors called leiomyomas do not express telomerase activity (11 samples tested), while the malignant uterine tumors called leiomyosarcomas do express telomerase activity (3 of 3 samples tested). Thus, the diagnostic methods of the invention also encompass a method for determining whether a uterine tumor is benign or malignant by analyzing a tumor tissue sample for telomerase activity and correlating the presence of telomerase activity with the presence of malignant tumor cells and the absence of telomerase activity with the presence of benign tumor cells.

In similar fashion, examination of pleural effusions in patients suspected of having lung cancer for telomerase activity can provide greater diagnostic benefit than conventional methodology. In some cases, X-ray analyses are not definitive, and a bronchoscope is often used to examine the lungs before surgery is recommended. One can take samples of tissues from the lung by literally brushing the inside lining of the lung during such a procedure, and analysis of the sample for the presence of telomerase activity provides a diagnostic for the presence of cancer cells if telomerase activity is present.

A variety of samples were examined for the presence of telomerase activity, as summarized in Table 2, below.

TABLE 2

Telomerase Activity in Human Tumors and Adjacent Tissues

| Tissue Type | Presence of Telomerase Activity |
| --- | --- |
| Gastrointestinal malignancies: | |
| Hepatocellular carcinoma (needle biopsy, frozen 3 months) | 1/1 |

TABLE 2-continued

Telomerase Activity in Human Tumors and Adjacent Tissues

| Tissue Type | Presence of Telomerase Activity |
| --- | --- |
| Colon cancer | 8/8 |
| Adjacent tissue | 0/7 |
| Tubular adenoma | 0/1 |
| Polyp | 0/1 |
| Squamous cell carcinoma (head and neck) | 14/16 |
| Adjacent tissue | 6/16 |
| Wilm's tuomor | 6/6 |
| Adjacent tissue | 2/6 |
| Neuroblastoma | 5/5 |
| Brain tumors | 6/8 |
| Myometrium | 0/10 |
| Leiomyoma (fibroids) | 0/11 |
| Leiomyosarcoma | 3/3 |
| Lung adenocarcinoma | 4/4 |
| Rhabdomyosarcoma | 1/1 |
| Hematological malignancies: | |
| Acute lymphocytic leukemia | 14/16 |
| Chronic lymphocytic leukemia | 2/2 |
| Lymphoma adult | 5/5 |

The results in Table 2 show that all 8 colon carcinomas exhibited telomerase activity while extracts of adjacent colonic mucosa without overt tumor tissue were negative for telomerase activity. Telomerase activity was not detected in an adenomatous colonic polyp or in a benign tubular adenoma from another patient. Squamous cell carcinomas of the head and neck (upper airway) were generally positive, as were some but not all of the adjacent tissue samples. Similar findings were made for the Wilm's tumor samples, where ⅔ of the adjacent tissue samples did exhibit low but detectable levels of telomerase activity relative to the tumor tissue extracts. Neuroblastoma, brain tumors, lung adenocarcinoma, rhabdomyosarcoma, hepatocellular carcinoma, lymphoma, and chronic lymphocytic leukemia samples were also telomerase positive. Of 16 bone marrow samples from children with acute lymphocytic leukemia, 14 samples were positive for telomerase activity.

Figure 1A:
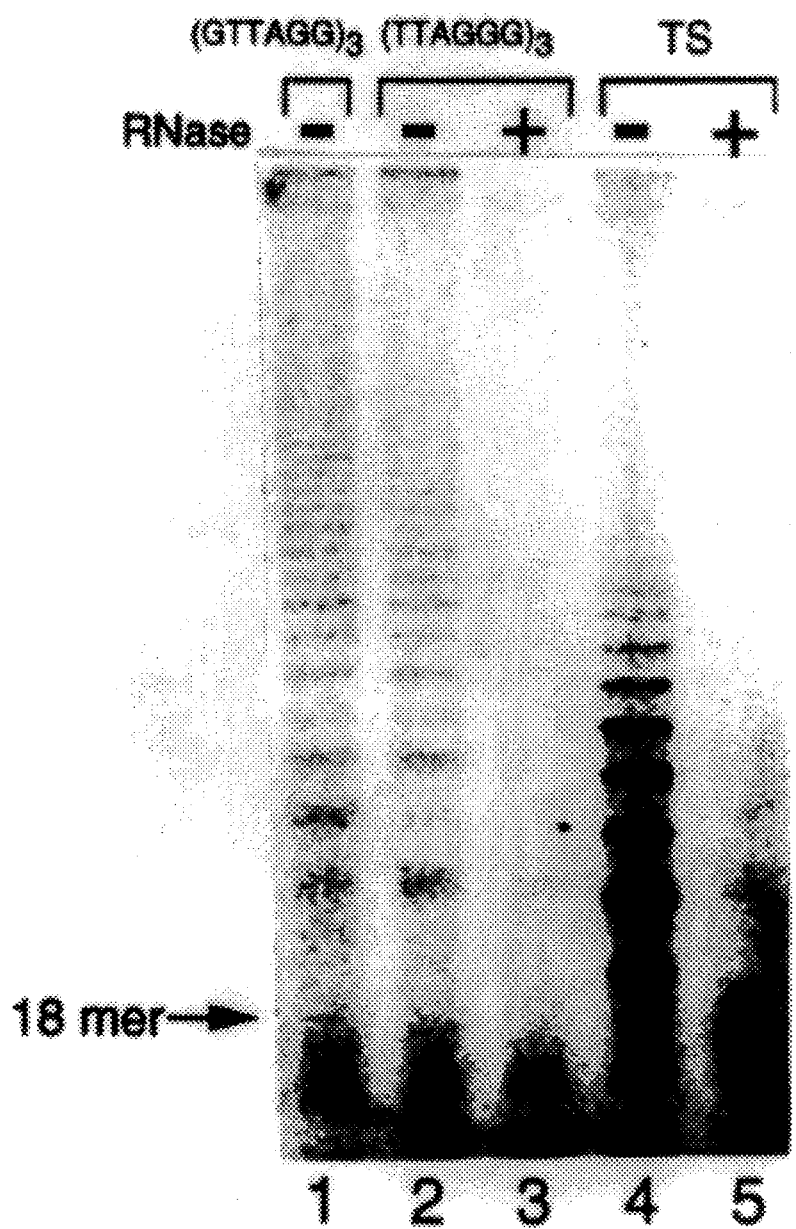
FIGS. 1A–1E show the improved results obtained using a detergent-based extraction method and telomerase activity assay as compared with the conventional methodology.
Figure 1B:
Figure 1C:
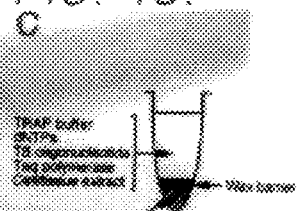
Figure 1D:
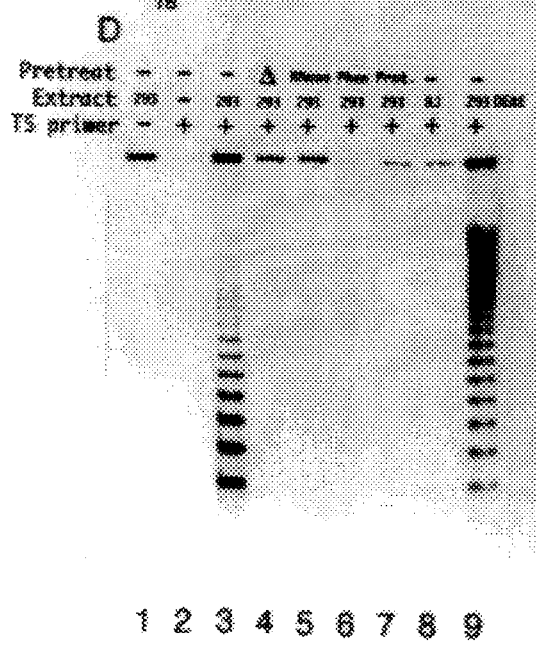
Figure 1E:
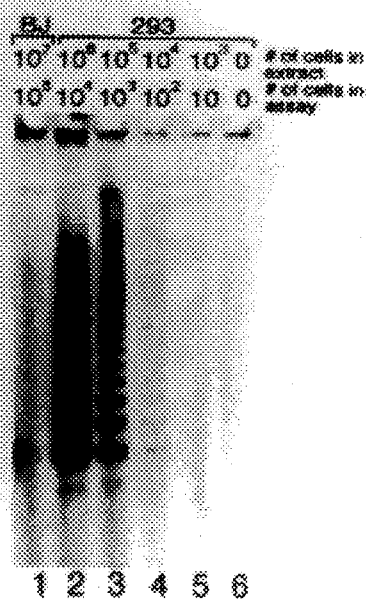
Figure 2A:
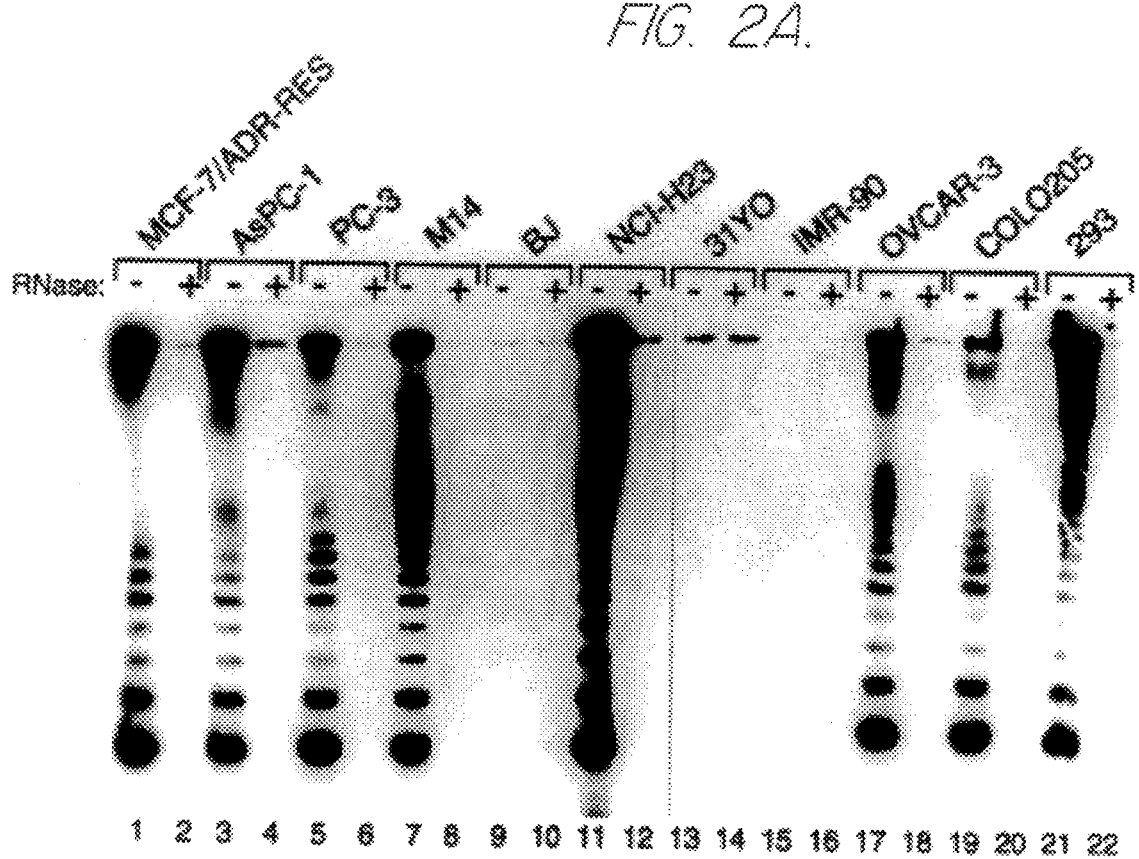
FIGS. 2A and 2B show a comparison of the TRAP assay (FIG. 2, part A) and a conventional assay (FIG. 2, part B) performed on the same 10 cell extracts, which were prepared from immortal cell lines and normal somatic cell cultures using the CHAPS detergent lysis method (see Examples 1 and 3, below).
Figure 2B:
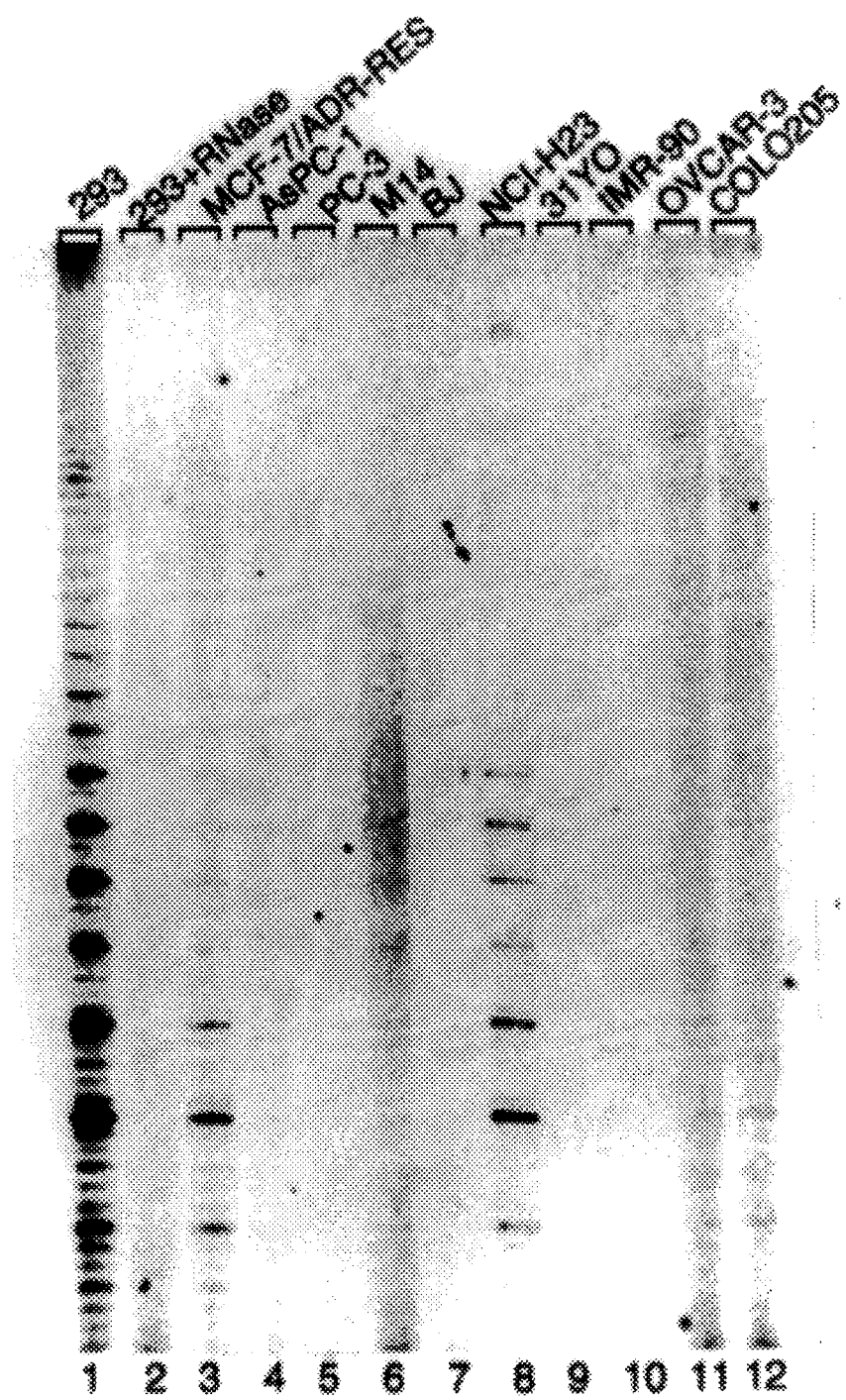

The TRAP assay method (described in Example 2, below) has also been used to test for telomerase activity in various immortal cell lines and normal somatic cell cultures from different tissues and individuals. FIG. 2 shows a comparison of TRAP assays (FIG. 2, part A) and conventional assays (FIG. 2, part B) performed on the same 10 cell extracts, which were prepared using the CHAPS detergent lysis method (see Examples 1 and 3, below). Some cell lines (293, MCF-7/ADR-RES, NCI-H23, OVCAR-3, COLO205, M14) show activity in both assays, others (AsPC-1 and PC-3) show activity only in the TRAP assay, and the normal somatic cell cultures (BJ, IMR-90 and 31YO) show no detectable activity by either assay. These results also demonstrate that the TRAP assay can detect telomerase activity in extracts that test negative by the conventional assay.

This survey was expanded to include a total of 74 immortal cell lines and 22 normal somatic cell cultures from 18 different tissues, and the results are summarized in Table 3 in Example 3, below. None of the normal somatic cell cultures displayed detectable telomerase activity in the TRAP assay. Of the 74 immortal cell lines, 68 were tumor-derived lines and 6 were cell lines transformed with viral oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells may not possess unlimited replicative capacity.

While the PCR-based TRAP assay has been described in detail above and is exemplified in the Examples below, the present method can be practiced using any method of detecting telomerase activity in a sample. While PCR provides for exponential accumulation of primer extension products, even linear accumulation of primer extension products can provide useful results. Thus, one can use a single primer and merely make many copies of a single strand of the duplex nucleic acid that is produced when PCR is employed.

Moreover, such copies can be made by means other than polymerase-mediated primer extension. Suitable methods include the ligase chain reaction (Barany, 1991, *Proc. Natl. Acad. Sci. USA* 88:189–193), nucleic acid sequence-based amplification (Compton, 1991, *Nature* 350:91–92), self-sustained sequence replication (Guatelli et al., 1990, *Proc. Natl. Acad. Sci. USA* 87:1874–1878), strand displacement amplification (Walker et al., 1992, *Proc. Natl. Acad. Sci. USA* 89:392–396), and branched DNA signal amplification (Urdea, 12 Sep. 1994, *Bio/Tech.* 12:926–928), although the latter method involves amplification of the signal produced upon probe hybridization to a target nucleic acid. As one example, DNA ligase can be used to ligate together two oligonucleotides hybridized to a template nucleic acid. If, as in PCR, the duplex nucleic acid is then denatured, then one can repeat the process of ligation and denaturation many times to accumulate many complementary copies of the original template, i.e., the extended telomerase substrate. If one additionally adds two other oligonucleotides complementary to the copy produced by ligation of the first two oligonucleotides on the extended telomerase substrate and selects those oligonucleotides such that DNA ligase can ligate the two together to form a copy of the original extended telomerase substrate, then one has the basic components of an LCR.

To illustrate, one could employ LCR to amplify an extension product of a telomerase substrate to detect telomerase activity in a sample using the following 4 oligonucleotide "ligomers":

LTS (5'-CCCAATCCGTCGAGCAGAGTTAG-3') (SEQ ID NO.1),

CLT (5'-TAACTCTGCTCGACGGATTCCC-3') (SEQ ID NO.2),

LC (5'-GGGTAACCCTAACCCTAACCC-3') (SEQ ID NO.3), and

LG (5'-GGTTAGGGTTAGGGTTAAA-3') (SEQ ID NO.4).

The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. A wide variety of such ligomers can be used in the method to minimize template-independent product formation. LCR amplification of telomerase extension products produces an amplified product of uniform size and so is conducive to quantitative analysis.

Moreover, a variety of different types of oligonucleotides can be used in telomerase activity assays. While the discussion above and Examples below illustrate assay methods with results obtained using deoxyribooligonucleotide telomerase substrates, controls, and primers or ligomers and with DNA ligases or polymerases, the present invention is not so limited. Thus, one can employ ribooligonucleotides or oligonucleotides that comprise one or more modified (i.e., synthetic or non-naturally occurring) nucleotides in the telomerase assay. In similar fashion, one can employ an RNA polymerase to extend a primer or to copy an extended telomerase substrate. These and other variations of the present method will be apparent to those of skill in the art upon consideration of this description of the invention.

Thus, the present invention can be used to detect the presence of cancer cells of any of a wide variety of types, including without limitation, solid tumors and leukemias including: apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell), histiocytic disorders, leukemia (e.g., B-cell, mixed-cell, null-cell, T-cell, T-cell chronic, HTLV-II-associated, lymphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia.

In the diagnostic methods of the invention, the assay will be conducted to determine whether an elevated level of telomerase is present. The phrase "elevated level" means that the absolute level of telomerase activity in the particular cell is elevated compared to normal somatic cells in that individual, or compared to normal somatic cells in other individuals not suffering from a disease condition.

Generally, any detectable level of telomerase activity is considered elevated in cells from normal, post-natal human somatic tissue. Although telomerase activity is present in germline cells, and low levels of telomerase activity can be detected in stem cells and certain hematopoietic system cells, such cells do not present problems for the practitioner of the present method. Germline cells can be readily distinguished and/or separated from human somatic tissue samples, and the telomerase activity present in stem cells and certain hematopoietic cells is present at such low levels that the few such cells present in somatic tissue samples will not create false positive signals from a telomerase activity assay. The detection of telomerase activity in somatic cells is indicative of the presence of immortal cells, such as certain types of cancer cells, and can be used to make that determination even when the cells would be classified as non-cancerous by pathology. Thus, the method of the present invention allows cancerous conditions to be detected with increased confidence before cells become visibly cancerous.

Those of skill in the art will also recognize that while the use of cell extracts is preferred for most purposes, one can also modify the method so that intact cells can be employed. In this embodiment, one treats intact cells with the telomerase substrate oligonucleotide, following which the oligonucleotide will be extended if the cell possesses functional telomerase activity. Established in situ PCR and LCR technology with a polymerase or ligase, a primer, and nucleoside triphosphates (if a polymerase is employed) are then used on fixed cells to amplify telomerase-extended substrate oligonucleotides. Telomerase positive cells can then be detected by microscopy utilizing, e.g., incorporation of a labelled nucleotide or oligonucleotide during primer extension.

The diagnostic tests of the invention can also be carried out in conjunction with other diagnostic tests. In some instances, such combination tests can provide useful information regarding the progression of a disease, although the present method for testing for telomerase activity provides much useful information in this regard. When the present method is used to detect the presence of cancer cells in a patient sample, the presence of telomerase activity can be used to determine where a patient is at in the course of progression of the disease, whether a particular tumor is likely to invade adjoining tissue or metastasize to a distant location, and whether an occurrence of cancer is likely to recur. Tests that may provide additional information in conjunction with the present method include diagnostic tests for the estrogen receptor, progesterone receptor, DNA ploidy, fraction of cells in S-phase, nodal status, Her-2/neu gene products, p53, p16, p21, ras, and other oncogenes.

The following examples describe specific aspects of the invention to illustrate the invention and provide a description of the method for those of skill in the art. The examples should not be construed as limiting the invention, as the examples merely provide specific methodology useful in understanding and practice of the invention.

EXAMPLE 1

Preparation of CHAPS-extracted Telomerase

In this Example, cell extracts prepared using a detergent-based extraction method were tested for telomerase activity using the conventional telomerase assay. The detergent lysis method involves the lysis of the cells in a sample in a lysis buffer composed of 0.01 to 5% of a non-ionic and/or a zwitterionic detergent. A wide variety of non-ionic and/or zwitterionic detergents can be employed in the method. Preferred non-ionic detergents include Tween 20, Triton X-100, Triton X-114, Thesit, NP-40, n-octylglucoside, n-dodecylglucoside, n-dodecylbeta-D-maltoside, octanoyl-N-methylglucamide (MEGA-8), decanoyl-N-methylglucamide (MEGA-10), and isotridecylpoly (ethyleneglycolether)$_n$, and preferred zwitterionic detergents include CHAPS (3-{(3-cholamidopropyl) dimethylammonio}-1-propane-sulfonate), CHAPSO (3-{(3-cholamidopropyl)dimethyl-ammonio}-2-hydroxy-1-propane-sulfonate), N-dodecyl-N,N-dimethyl-3-ammonio-1-propane-sulfonate, and digitonin, with CHAPS a particularly preferred detergent. While the exact amount of detergent is not critical, 0.5% is typically sufficient to observe enhanced extraction of telomerase activity.

The cell extracts were prepared from immortal 293 cells, which are known to express telomerase activity and are derived from human embryonic kidney cells transformed with fragments of adenovirus type 5 DNA. The cells were grown in Joklik's medium containing 5% to 10% fetal bovine serum and then collected by centrifugation (unless otherwise noted, the procedure below assumes that about 1 $\times 10^6$ cells were collected), washed once in PBS, pelleted at 10,000$\times$ g for 1 min. at 4° C., and resuspended in 1 mL of ice-cold wash buffer [10 mM HEPES-KOH (pH 7.5), 1.5 mM MgCl$_2$, 10mM KCl, 1 mM DTT, DEPC-treated water]. The cells were pelleted again and resuspended in ice-cold lysis buffer [10 mM Tris-HCl (pH 7.5), 1 mM MgCl$_2$, 1 mM EGTA, 1 mM PMSF, 5 mM β-mercaptoethanol, DEPC-treated water, 0.5% CHAPS (from Pierce), 10% glycerol] at a concentration of 20 μl of lysis buffer per $10^4$–$10^6$ cells (depending on the purpose of the experiment). The suspension was incubated on ice for 30 min. and then spun in a microultracentrifuge at 100,000$\times$ g for 30 min. at 4° C. The supernatant was removed to another tube, quick-frozen on dry ice, and stored at −70° C. These extracts typically contained a total protein concentration of 5 to 10 mg/ml, and the telomerase activity was stable to multiple freeze-thaws.

The procedure for and conditions of the conventional telomerase assay were as described by Counter et al., 1992; Counter et al., 1994, *EMBO J.* 11.:1921–1929; and Counter et al., 1994, *J. Virol.* 68:3410–3414, using oligonucleotide substrates at a concentration of 1 μM. See also Morin, 1989, *Cell* 59:521–529. The products were separated on an 8% polyacrylamide sequencing gel and exposed overnight to a Phosphorimager™ screen (Molecular Dynamics, Sunnyvale, Calif.). The results are shown in FIG. 1, part A. Note that product resolution differs between FIG. 1, part A, and FIG. 2, part B, because of different gel dimensions. The telomerase substrates used in the conventional assay were 5'-GTTAGGGTTAGGGTTAGG-3' (SEQ ID NO.5) (abbreviated as "(GTTAGG)$_3$"; see lane 1 of FIG. 1, part A); 5'-TTAGGGTTAGGGTTAGGG-3' (SEQ ID NO.6) (abbreviated as "(TTAGGG)$_3$"; see lanes 2 and 3 of FIG. 1, part A), and 5'-AATCCGTCGAGCAGAGTT-3' (SEQ ID NO.7) (abbreviated as "TS"; see lanes 4 and 5 of FIG. 1, part A). The extracts used in lanes 3 and 5 of FIG. 1, part A, were pretreated with RNase by incubation of 10 μl of extract with 0.5 μg of RNase (DNase-free, Boehringer Mannheim) for 10 min. at 25° C., which degrades the RNA component of telomerase and abolishes activity. Telomerase pauses after adding the first G of the G triplet, so the number of nucleotides added before the first pause (and thus the phasing of the ladder) is five for (GTTAGG)$_3$ (SEQ ID NO.5) (lane 1), four for (TTAGGG)$_3$ (SEQ ID NO.6) (lane 2), and two for the TS oligonucleotide (lane 4; see FIG. 1, part B, for a diagram of the TS extension products).

As demonstrated by FIG. 1, part A, the CHAPS-extracted telomerase activity functioned as predicted for human telomerase in a conventional telomerase activity assay. As shown in FIG. 1A, the non-ionic detergent-extracted activity produces the six nucleotide ladder of extension products (lanes 1, 2, and 4) characteristic of telomerase activity; there is a shift in product phase dependent upon the 3'-sequence of the oligonucleotide telomerase substrate (compare lanes 1, 2, and 4), as is expected for telomerase- mediated extension; that the activity extracted can extend a non-telomeric oligonucleotide previously shown to be a telomerase substrate (Morin, 1991, *Nature* 353:454–456; lanes 4 and 5) with 5'-TTAGGG-3' repeats (as confirmed using dideoxynucleotide chain termination sequencing); and that the activity was abolished by RNase treatment, as would be expected for telomerase activity (lanes 3 and 5; Greider and. Blackburn, 1985, *Cell* 43:405–413; Greider and. Blackburn, 1989, *Nature* 337: 331–337; Morin, 1989, *Cell* 59:521–529).

EXAMPLE 2

PCR Amplification of Telomerase Extension Products

This example illustrates the TRAP assay, a telomerase activity assay in which a DNA polymerase is used to mediate a primer extension reaction in a polymerase chain reaction. As shown in FIG. 1, part B, the reaction components include the telomerase substrate TS (the sequence of which is provided in Example 1, above), which telomerase extends by synthesizing telomeric repeats (shown by lower case sequence in FIG. 1, part B) and which also functions as the upstream primer in the PCR step, and the downstream primer CX, the structure of which is defined by its sequence 5'-(CCCTTA)$_3$CCCTAA-3' (SEQ ID NO.8). DNA synthesis during PCR is represented by broken arrows in FIG. 1, part B, and optimal annealing of the CX primer is shown using vertical lines, while asterisks indicate designed mismatches in the CX primer/extended telomerase substrate, which reduce interaction between the CX primer and unextended TS oligonucleotide telomerase substrate and so minimize primer-dimer (more accurately CX primer/TS dimer formation).

As noted above, telomerase is known to extend oligonucleotides of non-telomeric sequence, such as the TS oligonucleotide (Morin, 1991, *Nature* 353:454–456), and oligonucleotide substrate TS was used to avoid non-specific amplification due to PCR primer complementarity. As further modifications to avoid primer interaction, mismatches in the downstream primer CX, single stranded binding protein T4 gene 32 protein, hot start PCR, and an annealing temperature of 50° C. were used to conduct the telomerase activity assays described in this Example. Under these conditions, specific amplification occurs only if the oligonucleotide substrate has been extended with three or more 5'-TTAGGG-3' repeats, resulting in a six nucleotide ladder of TRAP assay products extending from 40 nucleotides (the first amplifiable telomerase product) up to the limit of gel resolution.

Yet another important modification that greatly improves the ease and efficiency of the TRAP assay relates to the development of a reaction buffer in which both telomerase and DNA polymerase can function. Use of this buffer allows one to employ a single tube set-up or format for the TRAP assay, as shown in FIG. 1, part C. This modification allows one to increase the specificity of primer extension, because the CX primer is initially separated from the rest of the reaction mix by a wax barrier, which melts only at the higher temperatures that mediate stringent hybridization conditions. The assay tubes were prepared by adding 2 µl of a 50 ng/µl suspension of CX primer (0.1 µg), which was spun to the bottom of the tube and evaporated until dry in a Speed-Vac™ centrifuge.

A trace amount of bromophenol blue was added to the CX primer suspension to monitor possible leakage through the wax barrier prior to thermal cycling. While the addition of dye for this purpose is in no way required for practice of the present invention, dye addition can be a convenient method for monitoring the integrity of a manufacturing process. Tubes were then heated at 70° C., and 7–10 µl of molten wax (Ampliwax™, Perkin-Elmer) was pipetted into the tube. After the wax was allowed to solidify at room temperature, the tubes were stored at 4° C. Tubes were warmed to room temperature before use. No effect on assay performance was observed using prepared tubes stored at 4° C. for up to two months; the expected shelf-life of such tubes (and kits comprising the same) is expected to be at least a year, even at ambient temperatures.

Reactions were typically carried out by the addition of 50 µl of TRAP reaction solution above the wax barrier. The reaction solution contained 20 mM Tris-HCl, pH 8.3, 1.5 mM MgCl$_2$, 63 mM KCl, 0.005% Tween 20, 1 mM EGTA, 50 µM each dNTP, 0.1 µg of TS oligonucleotide, 0.5 mM T4 gene 32 protein, 0.1 mg/ml BSA, 2 Units of Taq DNA polymerase (optionally use 2 Units of Taq treated with an equal volume of TaqStart™ antibody from Clontech to enforce hot start PCR), and 1–2 µl of a CHAPS cell extract. For radiolabeling of products, 0.2 to 0.4 µl of 10 µCi/µl $^{32}$P-dGTP and/or $^{32}$P-dCTP (3000 Ci/mmol) was added to the reaction. After 10 min. at 20° C. for extension of oligonucleotide TS by telomerase, the tubes were transferred to the thermal cycler (96 well Singleblock™ system, Ericomp) for 27 cycles, each cycle comprising incubation temperatures and periods of 94° C. for 30 sec., 50° C. for 30 sec., and 72° C. for 30 sec. to 1.5 min. The CX primer (0.1 µg) was liberated when the wax barrier melted at ~70° C. Those of skill in the art will recognize that the reaction times, temperatures, and buffers described in this Example can vary, depending upon the needs of the practitioner, the particular substrates and primers employed, and the source of the extract and DNA polymerase.

For instance, the telomerase extension reaction can be conducted at temperatures ranging from about 10 to about 42° C. The telomerase reaction time can vary widely, depending upon the number of primer extension steps employed, the amount of telomerase expected to be in the sample, and the time available to the practitioner. Typically, the telomerase reaction time will be between 5 and 60 min., but the time could be up to several hours. In similar fashion, the PCR cycles can be composed of cycle times and temperatures that vary widely. The simplest PCR cycle comprises a duplex nucleic acid denaturation step followed by a primer annealing and extension step. While denaturation is typically carried out by heating the reaction mixture, other methods, such as helicase treatment, can be used, and the heating method itself can be conducted at a wide range of temperature for any amount of time sufficient to denature but not damage the DNA. In similar fashion, the time and temperature of the primer annealing step depends to a great extent on the reaction buffer and primer sequence, concentration, and composition, as well as the specificity required by the practitioner, while the time and temperature of the primer extension step depends greatly upon the type of DNA polymerase employed. Those of skill in the art will recognize and understand that the present invention is not limited by the times, temperatures, and variations in buffer and other reaction components that can be employed in the method.

For analysis of the samples, one half of the reaction mixture was analyzed by electrophoresis in 0.5× TBE on 15% polyacrylamide non-denaturing gels. Visualization of the products was by ethidium bromide staining, silver staining, autoradiography, or Phosphorimager™ analysis (Molecular Dynamics, Sunnyvale, Calif.) of the gels. The results of the first set of assays described in this Example are shown in FIG. 1, part D. The set of assays was designed to test the specificity of the TRAP assay for telomerase activity.

Lane 1 of FIG. 1, part D, contains a control sample from which the TS oligonucleotide was omitted; lane 2 contains a control sample from which the cell extract was omitted; lane 3 contains a TRAP assay sample of an immortal 293 cell extract; lane 4 contains a sample of 293 extract pretreated by incubation for 10 min. at 65° C. to heat-inactivate the telomerase; lane 5 contains a sample of 293 extract pretreated by incubation for 10 min. with 0.5 μg of RNase (DNase-free, Boehringer Mannheim) at 25° C. to destroy the RNA component of telomerase; lane 6 contains a sample of phenol-extracted 293 extract (by mixing in an equal volume of a 1:1 phenol:chloroform mixture, vortexing for 30 sec., centrifuging to separate the phases, and collecting the aqueous phase); lane 7 contains a sample of 293 extract pretreated with protease by incubation of the extract (50 μl) with 5 μg of Bromelain protease (Boehringer Mannheim) for 10 min. at 37° C., removal of the Bromelin protease by incubation with an equal volume of carrier-fixed $\alpha_2$-macroglobulin (Boehringer Mannheim) for 30 min. at 25° C. with shaking and then centrifugation (to pellet the $\alpha_2$-macroglobulin/Bromelain complex) for 10 min. at 10,000× g, and collection of the supernatant for analysis; lane 8 contains a normal fibroblast BJ cell extract, which should lack telomerase activity; lane 9 contains a cell extract enriched for telomerase by DEAE chromatography (Morin, 1991, *Nature* 353:454–456).

As illustrated in FIG. 1, part D, the results of these multiple control experiments demonstrate that a positive signal in the TRAP assay requires a ribonucleoprotein in an immortal cell extract capable of extending the TS oligonucleotide with two or more 5'-TTAGGG-3' repeats, validating the assay for specific detection of telomerase activity.

To examine more closely the sensitivity of the TRAP assay, another set of assays was conducted to test the limits of detergent extraction and TRAP detection under the conditions employed. For extraction of different numbers of cells, the volume of lysis buffer was kept constant at 100 μl. The results of these assays are shown in FIG. 1, part E. Lane 1 shows the results of assaying about $10^5$ cell equivalents from an extract of $10^7$ normal fibroblast BJ cells; no activity was observed, as indicated by the absence of the ladder of bands. Lane 2 shows the results of assaying about $10^4$ cell equivalents from an extract of $10^6$ immortal 293 cells; telomerase activity was observed. Lane 3 shows the results of assaying about $10^3$ cell equivalents from an extract of $10^5$ 293 cells; telomerase activity was observed. Lane 4 shows the results of assaying about $10^2$ cell equivalents from an extract of $10^4$ 293 cells; telomerase activity was observed. Lane 5 shows the results of assaying about 10 cell equivalents from an extract of $10^3$ 293 cells; no activity was observed. Lane 6 shows the results of assaying a control with lysis buffer only; no activity was observed.

The limit of telomerase detection in $10^2$ cells was confirmed by TRAP assays of serial dilutions of an extract from $10^6$ 293 cells. This limit is a function of the TRAP assay conditions employed and should be considered a practical limit under the given set of conditions rather than an absolute limit of the sensitivity of the current method. For instance, use of primers CTR3 [(5'-CCCTAA-3')$_3$] (SEQ ID NO.9) or CTR4 [(5'-CCCTAA-3')$_4$] (SEQ ID NO.10) instead of CX (SEQ ID NO.8) further increases sensitivity, although these primers are more likely to interact with the unextended TS (SEQ ID NO.7) primer. The limit of sensitivity was also analyzed by titration of the synthetic telomerase product TS+4 (which contains oligonucleotide TS (SEQ ID NO7) followed by four telomeric repeats). Dilutions of TS+4 oligonucleotide were mixed with heat-treated (telomerase inactivated) 293 extract and analyzed in TRAP assays. In this analysis, the assay gave a clear positive signal from $10^6$ molecules of TS+4.

For the convenience of the practitioner, the following product information is provided. Reaction tubes were 0.2 ml Strip-ease™ tubes from Robbins Scientific (Sunnyvale, Calif.) and were autoclaved before use. All oligodeoxyribonucleotides were Ultrapure grade (HPLC-purified) obtained from Keystone Laboratory (Menlo Park, Calif.) and were suspended in DEPC-treated $H_2O$ at a concentration of 1 mg/ml. Taq DNA polymerase, Tween 20, and T4 gene 32 protein were purchased from Boehringer Mannheim. Radioisotopes were purchased from NEN-Dupont. The dNTPs were purchased from Pharmacia and were aliquoted, stored at −20° C., and thawed (no more than twice) before use. All other reaction components were molecular biology grade and purchased from Sigma, except when otherwise noted. Diethylpyrocarbonate (DEPC)-treated, de-ionized, sterile $H_2O$ was used routinely.

EXAMPLE 3

Relative Sensitivity of TRAP and Conventional Telomerase Assays—Assay of Telomerase Activity in Normal Somatic and Immortal Cells This Example describes telomerase assays conducted on cell samples of immortal cell lines and normal somatic cell cultures. Adherent cell cultures, such as BJ cells, a normal somatic cell culture of human skin fibroblasts, were grown to 80% confluency prior to extract preparation. The assays ($10^5$ cell equivalents per reaction) were conducted as described in Examples 1 and 2, above, and the results of the assay are shown in FIG. 2, parts A and B, and in Table 1, below. The TRAP assay results are shown in FIG. 2, part A; and the conventional assay results are shown in FIG. 2, part B. Assays were performed on the same 10 cell extracts, which were prepared using the CHAPS detergent lysis method (see Examples 1 and 2, above).

In FIG. 2, part A, the even-numbered lanes show the results for extracts pretreated with RNase, which should eliminate any telomerase activity in the sample. Lanes 1 and 2 show the results for breast carcinoma line MCF-7/ADR-RES; lanes 3 and 4 show the results for pancreatic carcinoma line AsPC-1; lanes 5 and 6 show the results for prostatic carcinoma line PC-3; lanes 7 and 8 show the results for melanoma line M14; lanes 9 and 10 show the results for normal foreskin fibroblast cell culture BJ; lanes 11 and 12 show the results for lung carcinoma line NCI-H23; lanes 13 and 14 show the results for normal stromal fibroblast cell culture 31YO; lanes 15 and 16 show the results for normal lung fibroblast cell culture IMR-90; lanes 17 and 18 show the results for ovarian carcinoma line OVCAR-3; lanes 19 and 20 show the results for colon carcinoma line COLO205; lanes 21 and 22 show the results for immortal kidney cell line 293. In FIG. 2, part B, the results for the conventional assays ($10^6$ cell equivalents per reaction) are shown. Lane 1 shows the results for immortal cell line 293; lane 2 shows the results for RNase pretreated 293; lanes 3–12 are the same as odd lanes 1–19 in FIG. 2, part A.

Some immortal cell lines (293, MCF-7/ADR-RES, NCI-H23, OVCAR-3, COLO205, M14) show activity in both assays, others (AsPC-1 and PC-3) show activity only in the TRAP assay, and the normal somatic cell cultures (BJ, IMR-90 and 31YO) show no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1, below. Each dividing cell culture was detergent-extracted and tested for telomerase activity using the TRAP assay. The specific immortal cell lines and normal somatic cell cultures are listed by tissue of origin. Immortal cell lines and normal somatic cell cultures tested were: (1) Skin—melanoma (LOXIMVI, M14, Malme-3M, UACC-62), normal fibroblasts (GFS, S37b, Malme-3, BJ), normal keratinocytes (1+ foreskin); (2) Connective—Fibrosarcoma (HT-1080); (3) Adipose—liposarcoma (SW872); (4) Breast—adenocarcinoma (MCF7, MCF-7/ADR-RES, MDA-MB-231), ductal carcinoma (T 47 D, MDA-MB-435), carcinoma (MDA-MB-157, MDA-MB-175-VI, MDA-MB-436, MDA-MB-468, ZR-75-1, ZR-75-30, UACC-812, UACC-893, BT-20, BT-474, BT-483, BT-549, HS578T, SK-BR-3, SCC70, SCC38, SCC202), normal epithelial and stromal cells (HME: 15, 17, 31, 32, 35); (5) Lung—carcinoma (NCI-H522, NCI-H23, A549, EKVK, 1299, H146, H69, NCI-H460, H358, H182), SV40 T-antigen transformed (IDH4, SW26-IG, SW-26-C4), normal fetal fibroblasts (GFL, IMR-90, Wi38); (6) Stomach—gastric carcinoma (KATO-III); (7) Pancreas —ductal carcinoma (SU.86.86), adenocarcinoma (AsPC-1, Capan-1); (8) Ovary—carcinoma (OVCAR-3, OVCAR-5, IGROV-1), adenocarcinoma (OVCAR-8); (9) Cervix—carcinoma (HeLa S3, C-33 A, HT-3), normal 1° epithelial cells; (10) Uterus—normal 1° endometrial cells; (11) Kidney—carcinoma (A498, CAKI-1), Ad5-transformed embryonic kidney cells (293); (12) Bladder—carcinoma (5637), transitional cell carcinoma (T24), squamous carcinoma (SCaBER), normal fetal (FHs 73851); (13) Colon —adenocarcinoma (COLO 205, SW-620, HCT-116); (14) Prostate—adenocarcinoma (PC-3, DU 145), SV40 transformed BPH fibroblasts (BPH-1), normal stromal fibroblasts (31YO), BPH fibroblasts (S52); (15) CNS—carcinoma (U251, SNB-75), glioblastoma (SF268); (16) Blood—leukemia (Molt4, HEL), T-cell leukemia (Jurkats), acute promyelocytic leukemia (HL-60), chronic myelogenous leukemia (K-562), histiocytic lymphoma (U-937); (17) Retina—SV40 transformed pigmented epithelium (AGO6096A); and (18) Joint: normal synovial fibroblast (HSF).

TABLE 3

Telomerase Activity in Mortal and Immortal Cells

| Tissue of Origin | Cell Type (Tumor/ Transformed/ Normal/) | Telomerase Activity (# positive/ # tested) |
|---|---|---|
| Skin | Tumor | 4/4 |
| | Normal | 0/5 |
| Connective | Tumor | 1/1 |
| Joint | Normal | 0/1 |
| Adipose | Tumor | 1/1 |
| Breast | Tumor | 22/22 |
| | Normal | 0/8 |
| Lung | Tumor | 0/10 |

TABLE 3-continued

Telomerase Activity in Mortal and Immortal Cells

| Tissue of Origin | Cell Type (Tumor/ Transformed/ Normal/) | Telomerase Activity (# positive/ # tested) |
|---|---|---|
| | Transformed | 2/3 |
| | Normal | 0/3 |
| Stomach | Tumor | 1/1 |
| Pancreas | Tumor | 3/3 |
| Ovary | Tumor | 4/4 |
| Cervix | Tumor | 0/3 |
| | Normal | 0/1 |
| Uterus | Normal | 0/1 |
| Kidney | Tumor | 2/2 |
| | Transformed | 1/1 |
| Bladder | Tumor | 3/3 |
| | Normal | 0/1 |
| Colon | Tumor | 3/3 |
| Prostate | Tumor | 2/2 |
| | Transformed | 0/1 |
| | Normal | 0/2 |
| CNS | Tumor | 3/3 |
| Retina | Transformed | 1/1 |
| Blood | Tumor | 6/6 |

None of the normal somatic cell cultures displayed detectable telomerase activity in the TRAP assay. Of the 74 immortal cell lines, 68 were tumor-derived lines and 6 were cell lines transformed with vital oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells will not replicate indefinitely.

EXAMPLE 4

Standard Operating Procedure for Telomeric Repeat Amplification Protocol (TRAP)

This Example provides a step-by-step protocol for performing the TRAP assay, in five parts: (A) Work station set-up; (B) Precautions; (C) Micro-extraction; (D) Quantitative Assay; and (E) Analysis. The method described provides for a quantitative analysis of the activity, and while a number of recommendations are made, those of skill will recognize that, depending on the conditions used and nature of the results desired, not all recommendations need be followed in all circumstances.

As the results described in the preceding Examples demonstrate, the PCR-based TRAP assay offers significant improvements over currently available methods for measuring telomerase activity in a sample. Other variations of the TRAP assay, however, also offer significant advantages. In particular, one can quantitate the telomerase activity in a sample by providing the number of telomerase products generated per unit time. To understand the nature of these improvements, however, one first might consider more carefully the results obtained using the assay described in Example 2, as depicted in FIGS. 1 and 2. As one can note from those Figures, the ladder of bands produced upon gel electrophoresis of the assayed samples extends up the gel. Such results might reflect the number of repeats added by telomerase during the telomerase-mediated extension reaction or could result from staggered binding of primers during PCR amplification.

The phrase "staggered binding" refers to the binding of a primer to a sequence in an extended telomerase substrate in a manner that leaves the 3'-end of the extended telomerase substrate recessed and therefore available for extension by DNA polymerase. DNA polymerase can then add nucleotides to the 3'-end of the extended telomerase substrate, creating molecules longer than those produced in the telomerase-mediated extension step. To determine whether staggered binding was occurring in reactions such as those described in Example 2, synthetic oligonucleotides representing discrete telomerase extension products, e.g., TS+4 (TS (SEQ ID NO.7) plus four telomeric repeats), were used to develop specific amplification conditions. Even under high stringency, staggered annealing of the downstream primer occurred (e.g., annealing by 3 of the 4 repeats). Hence PCR amplification of a discrete telomerase extension product yielded a six nucleotide ladder of PCR products increasing in size up to the limit of gel resolution. Thus, TRAP assay products produced using a primer such as CX (SEQ ID NO.8) are not directly reflective of the length distribution of telomerase products generated in the assay, due to the staggered binding of primers to templates during the primer extension reactions.

To prevent such interaction from generating products with more repeats than telomerase added to the substrate, one can employ a novel "anchored" primer as the downstream primer in the assay. The oligonucleotide ACT is a 24 nucleotide oligonucleotide primer that comprises a 6 nucleotide anchor sequence at its 5'-end and three repeats of CTR (C-rich telomeric repeat) sequences (5'-CTAACC-3'). For purposes of the present invention, an anchor sequence is a 5'-terminal sequence of a PCR primer that is non-complementary and non-identical to a telomeric repeat sequence and that prevents the PCR product from "growing" on itself as observed when the primer pairs TS/CTR4 (SEQ ID NO.7/SEQ ID NO.10) or TS/CX (SEQ ID NO.7/SEQ ID NO.8) are employed.

A wide variety of anchor sequences can be employed. In one embodiment, the anchor sequence is the sequence of the telomerase substrate used in the telomerase-mediated extension step of the method, providing a "TS-anchored" primer. The anchored primer would thus comprise, in the 5'-to-3' direction, a telomerase substrate sequence and two or more complementary copies of the telomeric repeat sequence. By employing such a primer, one can practice the present method in what is essentially a "one primer" mode, because after the first round of primer extension, excess unextended telomerase substrate in the reaction mixture can prime the synthesis of both strands of the complex formed as a result of the first round of primer extension.

By using the primers TS (SEQ ID NO.7) and ACT (SEQ ID NO.11) (or another anchored primer) in the TRAP assay, one can deduce the Most Processive Product (MPP) of the telomerase in a given extract. The use of an anchored primer such as ACT prevents the growth of telomerase products into longer versions during PCR. With the ACT primer, the slowest migrating band reflects directly the length of the MPP of the original telomerase products before the PCR. The ACT primer is particularly preferred for purposes of the present invention in that it is more resistant to the types of primer-dimer interactions observed between TS and primers such as CX or CTR4.

The TRAP assay also provides a variety of means to quantitate the amount of telomerase in a sample, although for most purposes, a qualitative result (telomerase activity present or absent) is sufficient. One important means for obtaining quantitative information is the use of a control oligonucleotide template added to each reaction mixture in a known amount. An illustrative control oligonucleotide comprises, in 5'-to-3' order, a telomerase substrate sequence, a spacer sequence (optional: the presence of a spacer sequence, preferably 3 bases, but which can be any sequence of nucleotides or length, can alter spacing of the ladder produced by electrophoresis of reaction products produced from telomerase positive samples), a telomeric repeat sequence (typically present in multiple, i.e., 2 to 50, copies), and a sequence complementary to the primer used in the assay (and so which may simply be a portion of the telomeric repeat sequence and if the primer includes an anchor sequence, then optionally a sequence complementary to the anchor sequence). Of course, an oligonucleotide complementary to the control sequence defined above can also serve as the control sequence, and a double-stranded control nucleic acid can also be employed.

Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products. Use of an internal control not only facilitates the determination of whether the assay was conducted properly but also facilitates quantitation of the telomerase activity present in the sample. The control oligonucleotide can also be conveniently packaged into a kit with other reaction components. The detailed protocol for conducting TRAP assays using the ACT primer and internal control follows.

Work Station Set-up

An important factor in the set-up of the TRAP assay is the environment where the initial reaction mixtures are made prior to the PCR step. The ideal environment is free of contaminating ribonucleases and PCR amplified DNA products, which can cause erroneous negative and positive results, respectively. A major source of PCR product (and RNase) contamination can be the person performing the experiment, who should maintain high standards of personal hygiene and avoid generation of aerosols of PCR products when opening or pipetting PCR products or disposing of gel buffer after the electrophoresis of PCR products. A positive air displacement hood, which blows in filtered air over the sample toward the investigator, is ideal. Separate solutions, pipettes, tubes, and tips should always be used and kept inside the hood. Work space should be wiped with 10% bleach prior to set-up of the reaction, and the hood should be routinely UV-irradiated when not in use. Also, barrels of pipettes should be periodically soaked in 10% bleach, even when aerosol-resistant tips are used. The investigator should wear gloves and a disposable lab coat with elastic wrist straps; the lab coat should be periodically changed.

A dedicated work area for setting up TRAP reaction can be prepared by placing an acrylic shield of 45.7 cm (L)×30.5 cm (W)×61 cm (H) size from VWR (cat. #56615-848) on a standard cubby-hole type desk. The top of the desk is covered either by a board or heavy cloth, and the front is blocked by the shield. This arrangement creates dead-air space, where the contaminants are prevented from falling into the working area from outside and the samples are physically blocked from the investigator. All the solutions, pipettes, tips, and tubes are kept inside the station, and the working area is routinely UV irradiated by a short-wave UV lamp mounted on the top of the station (Black Ray UV lamp, XX-15S, VWR cat#36575-059).

(B) Precautions

As noted above, and because the TRAP assay incorporates both PCR amplification and use of in vitro activity of a ribonucleoprotein (telomerase), there is a need for extreme caution to prevent PCR-product contamination (DNA) and RNase contamination, both of which can be detrimental to the assay. The following basic precautions can be followed in all steps of the assay protocol, including the telomerase extraction and PCR amplification steps, to avoid problems: (1) use DEPC-treated $H_2O$ for all solutions, and aliquot the solutions in small amounts before use; (2) keep the assay solutions (PCR buffer, CHAPS extraction buffers, dNTPs, Taq polymerase, etc.) separate from other reagents in the laboratory; (3) wear gloves; (4) use a dedicated set of pipettors for the assay and aerosol-resistant tips (ARTs); and (5) do not analyze the amplified samples in the same area where the samples are prepared (i.e., do not open PCR tubes after the PCR amplification on the same bench where the assay reagents and pipettes/tips are located; instead use other pipettors (optionally without ARTs) at a location away from the PCR bench).

(C) Micro-extraction

The material requirements for the lysis buffer used in the micro-extraction procedure are shown below.

| Lysis Buffer (0.54 CHAPS* or CHAPSO*) | | | |
|---|---|---|---|
| Stock | Final | 0.5 mL | 10 mL |
| 1 M Tris-HCl pH 7.5 | 10 mM | 5 µl | 100 µl |
| 1 M MgCl2 | 1 mM | 0.5 µl | 10 µl |
| 0.5 M EGTA | 1 mM | 1 µl | 20 µl |
| *0.1 M PMSF | 0.1 mM | 0.5 µl | 10 µl |
| *BME (14.4 M) | 5 mM | 0.17 µl | 3.5 µl |
| 10% Detergent | 0.5% | 25 µl | 500 µl |
| 100% Glycerol | 10% | 50 µl | 1 mL |
| DEPC $H_2O$ | | 417.83 µl | 8.36 mL |

*The CHAPS or CHAPSO detergent should be added just before use of the lysis buffer. In addition, one should add 0.1 M PMSF (1 µl) and beta-mercaptoethanol (0.35 µl) to 1 ml of lysis buffer just prior to performing the extraction step.

The micro-extraction procedure involves the following steps:

1. Establish the cell count, pellet the cells, wash the cells twice in PBS (Ca and Mg—free), repeller, and remove PBS.
2. Suspend cells in wash buffer and repellet the cells.
3. Remove wash buffer, resuspend cell pellet in 20 µl of lysis buffer per $10^6$–$10^4$ cells (depending on the application).
4. Incubate the cells on ice for 30 min.
5. Spin the cells in a microcentrifuge (Eppendorf) at 10000× g for 20 min. at 4° C.
6. Remove extract to another tube, use 1 to 2 µl per TRAP assay; one can quick-freeze the remainder on dry-ice and store at −70° C., if desired.

(D) Quantitative Assay

The following materials are recommended for the assay: TRAP wax-barrier reaction tubes; ACT primer (5'-GCGCGG[CTAACC]$_3$-3' (SEQ ID NO.11), 100 ng/tube); 2.5 mM dNTPs (Pharmacia); end-labeled TS Primer (M2, 0.1 mg/ml); Taq polymerase (Boehringer Mannheim); and 10× TRAP Buffer.

| 10X TRAP Buffer | |
|---|---|
| Components | For 5 ml |
| 200 mM Tris-HCl,pH 8.3 | 1 ml (1 M Tris-Cl pH 8.3) |
| 15 mM MgCl$_2$ | 75 µl (1 M MgCl$_2$) |
| 630 mM KCl | 3.15 ml (1 M KCl) |
| 0.05% Tween 20 | 25 µl (Boehringer Mannheim) |
| 10 mM EGTA | 500 µl (0.1 M EGTA) |
| 1 mg/ml BSA | 250 µl (20 mg/ml) |
| ACT-IC | 0.77 to 1.54 pg (5–10 amol/50 µl reaction mixture |

ACT-IC is an internal control oligonucleotide of sequence: 5'-AATCCGTCGAGCAGAGTTAGCCCGGTTAGGGTT-AGGGTTAGCCGCGC-3' (SEQ ID NO.12), specifically designed for the M2 (TS) telomerase substrate (and PCR primer) and the ACT primer. Note that the presence of the sequence complementary to the anchor sequence is optional, and that it may be desirable in some instances not to have this sequence present in the internal controls. Presence of this oligonucleotide internal control (the final amount of ACT-IC will be 5-to-10 amol [$10^{-3}$ fmol] per 50 µl TRAP reaction) will result in a specific PCR amplification product that appears as a band on a gel between the first and second products of the TRAP assay, regardless of RNase treatment or no-extract control. This internal control band can be used to normalize the PCR amplifications from different samples, and to calculate the number of telomerase products generated when used in combination with end-labeled TS oligonucleotide substrate/primer (see Analysis, below).

To prepare a reaction mixture, the following materials are mixed in the TRAP reaction tube, which contains 0.1 µg of dried ACT primer under a wax barrier.

| Material | For 50 µl Total Volume |
|---|---|
| 10X TRAP Buffer | 5 µl |
| 2.5 mM dNTPs(Pharmacia) | 1 µl |
| *Primer (0.1 mg/ml TS) | 1 µl |
| Taq (Boehringer Mannheim) | 0.4 µl (2 Units) |
| Telomerase Extract | 2 µl |
| $H_2O$ | 40.6 µl |

*For a quantitative TRAP assay, one can end-label the TS substrate/primer with, e.g., [$^{32}$P]-gamma-ATP using T4 polynucleotide kinase, or with other reagents, such as 5'-biotin, digoxigenin, fluorescein or another fluorophore, depending on the particular detection and quantification system to be employed.

Optional ingredients include 0.2 µl of T4 gene 32 protein (5 mg/ml, available from Boehringer Mannheim), and 0.4 µl of TaqStart™ antibody (available from Clontech). The reaction is carried out according to the following steps:

1. incubate the reaction mixture at room temperature (20° C.) for 10 min.;
2. incubate the reaction mixture at the following temperatures for the times indicated to conduct the PCR: 94° C./30 sec., 60° C./30 sec., and 72° C./30 sec.; repeat this three-step cycle to conduct 20–30, preferably 27, cycles;
3. add loading dye containing bromophenol blue and xylene cyanol, and subject samples to 10–15% non-denaturing PAGE in 0.6× TBE, until the bromophenol blue runs off the gel (molecular marker V from Boehringer Mannheim is a good DNA marker for this gel); and
4. observe product formation, e.g., by Phosphorimager™ screen (for a radioactive label) or another appropriate means of detection.

(E) Analysis

Using the protocol outlined above and assuming that the internal control is amplified with the same efficiency as the telomerase substrate extension products, one can estimate the number of telomerase molecules generated in a given reaction, according to the formula (T=total counts per lane):

[(T TRAP Products-T ACT-IC)/T ACT-IC]×(number of molecules of ACT-IC added)

The resulting number is the number of molecules of telomerase products generated for a given incubation time (usually 10 min.). This calculation is valid only if the TS substrate was end-labeled and does not apply to a TRAP protocol in which direct incorporation of radioactive dNTPs is used for detection (even if the ACT primer and internal controls are utilized). These conditions also account for possible variations in PCR amplification between samples and so provide a standard measurement.

If an extract has high levels of telomerase activity, then the signal from the ACT-IC can be more difficult to detect, because this method involves a "competitive PCR" in which the telomerase products and the internal controls are both competing for the same primers. In other words, the primers should be present in excess over templates for the quantitative analysis to be accurate. Therefore, if a sample has very high levels of telomerase activity, one can dilute the extract so that the PCR primers are not limiting. Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products.

EXAMPLE 5

Analysis of Telomerase Activity in Human Normal and Abnormal Tissues

This Example describes the preparation of tumor and tissue samples from human donors and the analysis of those samples with the TRAP assay.

Small pieces of fresh or flash-frozen tissue (about 100 mgs or less) were placed in Kontes tubes (VWR cat. #KT749520-0000) containing 200–250 μl of ice cold CHAPS lysis buffer and dispersed with the accompanying matching disposable pestle rotating at about 450 rpm (Black & Decker cordless drill, model CD1000). After homogenization (avoiding excess heat), the lysates were incubated on ice for 10 min. and then centrifuged at 16,000× g for 20 min. at 4° C. The supernatants were then collected and flash-frozen in an EtOH-dry ice bath and stored at −80° C. until analysis.

Aliquots of the extracts containing about 6 μg of protein (as measured using the BCA protein assay kit from Pierce Chemical Co.) were used for each TRAP assay. Assays were conducted and results analyzed as described in Examples 2 and 3, above, except that 30 PCR cycles were conducted.

One set of samples was prepared for assay to demonstrate that the TRAP assay was reliable for analysis of telomerase activity in human tissue samples subjected to a variety of experimental manipulations. In these tests, normal somatic (telomerase negative) and germline (telomerase positive) tissues were obtained from a male who died of natural causes (heart attack). Immediately postmortem this individual was at room temperature for approximately 3 hours and then maintained for an additional 9 hours at 4° C. prior to autopsy. The results of the tests are shown in FIG. 3.

As expected, telomerase activity was present in testicular tissue but not in other tissues examined (lanes 1 and 5–11). Preincubation of the testicular tissue extract with RNase to destroy the RNA component of telomerase abolished the PCR ladder (lane 2). To determine the stability of telomerase activity, a portion of the testicular sample was incubated at room temperature for 18 hours and then assayed; the sample retained activity (lane 3). Telomerase activity was still retained in an extract from a human primary breast tumor (lane 12) even after 10 cycles of freeze/thawing (lane 14). These tests demonstrated that telomerase activity is relatively stable and that negative results are likely to represent the absence of telomerase activity rather than its loss.

Figure 4:
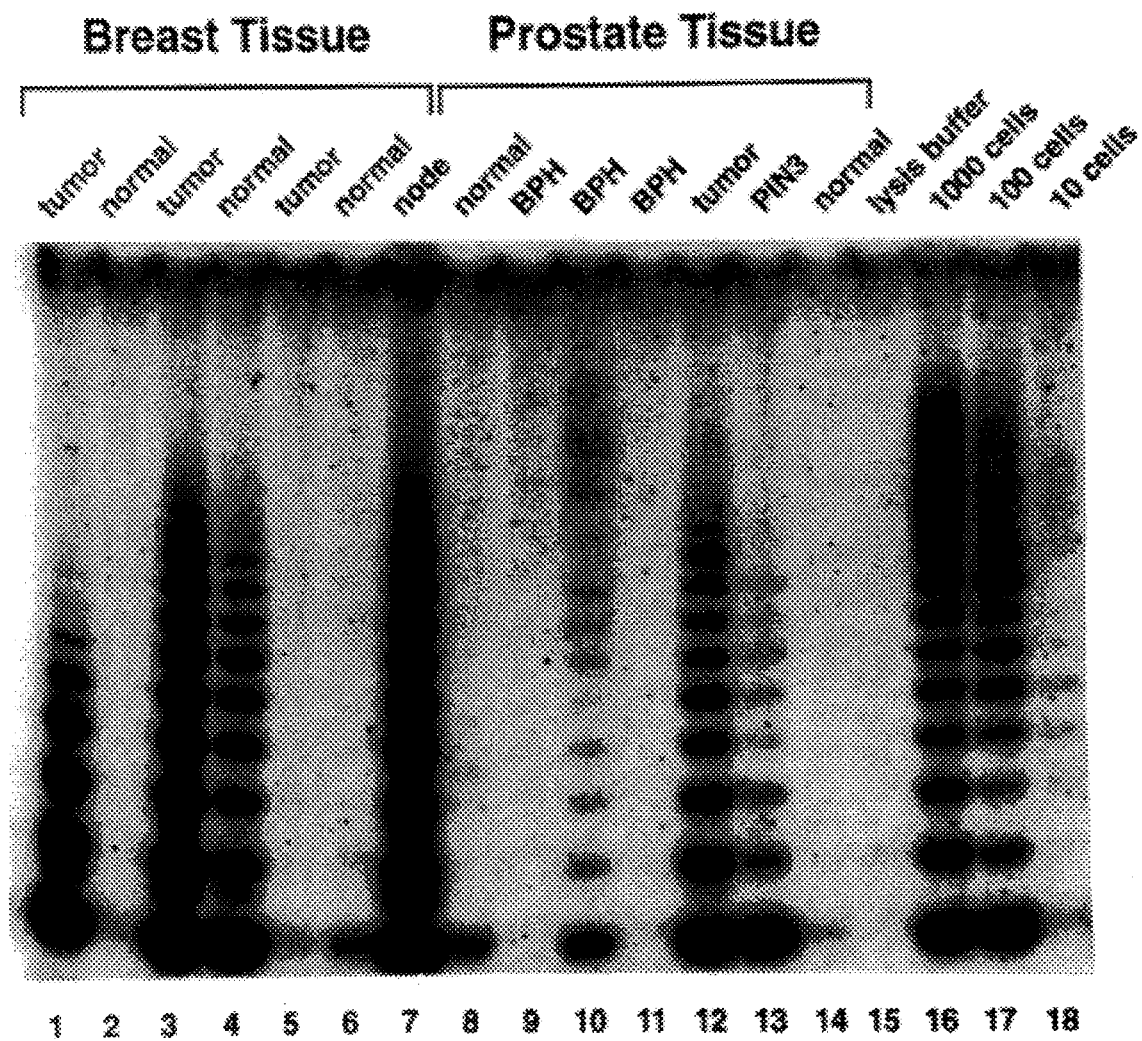
FIG. 4 shows the results of telomerase assays conducted on samples of breast and prostate tissues. Most tumors were positive for telomerase activity (but see lane 5, a telomerase-negative, axillary node-negative breast cancer tissue sample), while adjacent tissue (shown as "normal") was generally negative for telomarase activity (but see lane 4, a telomerase-positive sample from apparently normal adjacent tissue). A lymph node sample from a node-positive breast cancer patient is shown in lane 7. Prostatic tissue samples are shown in lanes 8–13. One benign prostatic hyperplasia tissue sample and some of the prostatic intraepithelial neoplasia tissue samples also tested positive for telomerase activity (lanes 10 and 13) but with relatively weak signals. Analysis of extracts from cell equivalents of a telomerase-positive breast tumor cell showed that telomerase activity can be detected from as few as 10 cell equivalents (lanes 16–18).

FIG. 4 shows the results of telomerase assays conducted on samples of breast and prostate tissues. Most tumors were positive for telomerase activity (but see lane 5, a telomerase-negative, axillary node-negative breast cancer tissue sample), while adjacent tissue (shown as "normal") was generally negative for telomerase activity (but see lane 4, a telomerase-positive sample from apparently normal adjacent tissue). A lymph node sample from a node-positive breast cancer patient is shown in lane 7. Prostatic tissue samples are shown in lanes 8–13. One benign prostatic hyperplasia tissue sample and some of the prostatic intraepithelial neoplasia tissue samples also tested positive for telomerase activity (lanes 10 and 13) but with relatively weak signals. The weakness of the signal may be due to the low percentage of telomerase-positive cells in the sample. The present method can readily detect telomerase activity in a sample in which less than 1% of the cells express the activity. Analysis of extracts from cell equivalents of a telomerase-positive breast tumor cell showed that telomerase activity can be detected from as few as 10 cell equivalents (lanes 16–18).

The foregoing examples describe various aspects of the invention and how the method can be practiced. The examples are not intended to provide an exhaustive description of the many different embodiments of the invention. All publications and patent applications cited above are hereby incorporated herein by reference as if each individual publication or patent application were specifically and individually indicated to be incorporated by reference. Thus, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for detecting whether a human breast, prostate, colon, or lung tissue sample contains cancerous cells, said method comprising
   (a) preparing a cell extract from said tissue sample;
   (b) incubating an aliquot of said cell extract in a reaction mixture comprising a telomerase substrate and a buffer in which telomerase can catalyze the extension of said telomerase substrate;
   (c) determining whether said telomerase substrate has been extended in step (b) by addition of telomeric repeat sequences; and
   (d) correlating presence of cancerous cells in said sample with the addition of telomeric repeat sequences to said telomerase substrate and absence of cancerous cells in said sample with no addition of telomeric repeat sequences to said telomerase substrate.

2. The method of claim 1, wherein said breast tissue sample is removed from tissue adjacent to a tumor.

3. The method of claim 1, wherein said breast tissue sample is removed from an individual previously diagnosed as having axillary node negative breast cancer.

4. The method of claim 1, wherein said prostate tissue sample is removed from tissue adjacent to a location at which cancer cells are known to have been present.

5. The method of claim 1, wherein said prostate tissue sample is removed from an individual previously diagnosed as having benign prostatic hyperplasia.

6. The method of claim 1, wherein said prostate tissue sample is removed from an individual previously diagnosed as having prostatic intraepithelial neoplasia.

7. The method of claim 1, wherein step (b) further comprises amplifying any extended telomerase substrates in said reaction mixture by an amplification method selected from the group consisting of polymerase chain reaction and ligation chain reaction.

8. A method for determining prognosis of a patient known to have cancer by detecting whether a tissue sample contains cancerous cells, said method comprising (a) preparing a cell extract from said tissue sample;

(b) incubating an aliquot of said cell extract in a reaction mixture comprising a telomerase substrate and a buffer in which telomerase can catalyze the extension of said telomerase substrate;

(c) determining whether said telomerase substrate has been extended in step (b) by addition of telomeric repeat sequences;

(d) correlating presence of cancerous cells in said sample with the addition of telomeric repeat sequences to said telomerase substrate and absence of cancerous cells in said sample with no addition of telomeric repeat sequences to said telomerase substrate; and (e) correlating a negative prognosis in said patient with a presence of cancerous cells in said sample, and a positive prognosis in said patient with an absence of cancerous cells in said patient.

9. The method of claim 8 wherein said tissue sample is an axillary-node breast tissue sample.

10. The method of claim 8 wherein said tissue sample is a prostate tissue sample.

11. The method of claim 10 wherein said prostate tissue sample is removed from a patient previously diagnosed as having prostatic intraepithelial neoplasia.

12. The method of claim 10 wherein said prostate tissue sample is removed from a patient previously diagnosed as having benign prostate hyperplasia.

* * * * *